US011497818B2

(12) United States Patent
Lux et al.

(10) Patent No.: US 11,497,818 B2
(45) Date of Patent: Nov. 15, 2022

(54) ULTRAFINE NANOPARTICLES COMPRISING A FUNCTIONALIZED POLYORGANOSILOXANE MATRIX AND INCLUDING METAL COMPLEXES; METHOD FOR OBTAINING SAME AND USES THEREOF IN MEDICAL IMAGING AND/OR THERAPY

(71) Applicants: NANOH, Saint-Quentin-Fallavier (FR); UNIVERSITE LYON 1 CLAUDE BERNARD, Villeurbanne (FR); INSTITUT NATIONAL DES SCIENCES APPLIQUEES DE LYON, Villeurbanne (FR)

(72) Inventors: François Lux, Lyons (FR); Olivier Tillement, Fontaines Saint-Martin (FR); Maxime Saint Jean, Caluire et Cuire (FR); Pierre Mowat, Venissieux (FR); Pascal Perriat, Lyons (FR); Stéphane Roux, Cheneycey Buillon (FR); Anna Mignot, Lyons (FR)

(73) Assignees: NANOH, Saint-Quentin-Fallavier (FR); UNIVERSITE LYON 1 CLAUDE BERNARD, Villeurbanne (FR); INSTITUT NATIONAL DES SCIENCES APPLIQUEES DE LYON, Villeurbanne (FR)

(\*) Notice: Subject to any disclaimer, the term of this patent is extended or adjusted under 35 U.S.C. 154(b) by 180 days.

(21) Appl. No.: 15/987,500

(22) Filed: May 23, 2018

(65) Prior Publication Data
US 2018/0264145 A1 Sep. 20, 2018

Related U.S. Application Data

(60) Continuation of application No. 15/677,167, filed on Aug. 15, 2017, now Pat. No. 10,987,435, which is a
(Continued)

(30) Foreign Application Priority Data

Apr. 30, 2010 (FR) ..................... 1053389

(51) Int. Cl.
*A61K 49/18* (2006.01)
*A61K 9/14* (2006.01)
(Continued)

(52) U.S. Cl.
CPC ............ *A61K 49/1824* (2013.01); *A61K 9/14* (2013.01); *A61K 41/0038* (2013.01);
(Continued)

(58) Field of Classification Search
None
See application file for complete search history.

(56) References Cited

U.S. PATENT DOCUMENTS

2006/0233704 A1\* 10/2006 Maecke ............. A61K 49/0002
424/1.49
2007/0281324 A1 12/2007 Perriat et al.
(Continued)

FOREIGN PATENT DOCUMENTS

FR 2867180 9/2005
FR 2922106 4/2009
(Continued)

OTHER PUBLICATIONS

Mandon et al. (Imaging Med, 2(2), 211-223, 2010) Multifunctional gadolinium oxide . . . .\*
Weinmann et al. (American Journal of Roentgenology. 1984:142: 619-6241 Characterstics of Gadolinium-DTPA Complex . . . .\*
Barbillon, et al., "How Nanoparticles Encapsulating Fluorophores Allow a Double Detection of Biomolecules by Localized Surface Plasmon Resonance and Luminescence," *Nanotechnology*, vol. 19, No. 3, pp. 35705, (2008).
Bridot, et al., "Hybrid Gadolinium Oxide Nanoparticles Combining Imaging and Therapy," *Journal of Materials Chemistry*, vol. 19, pp. 2328-2335, (2009).
Bridot, et al., "Hybrid Gadolinium Oxide Nanoparticles: Multimodal Contrast Agents for in Vivo Imaging," *Journal of the American Chemical Society*, vol. 129, No. 16, pp. 5076-5084, (2007).
(Continued)

*Primary Examiner* — Tigabu Kassa
(74) *Attorney, Agent, or Firm* — Hoxie & Associates LLC

(57) ABSTRACT

The invention relates to novel biocompatible hybrid nanoparticles of very small size, useful in particular for diagnostics and/or therapy.
The purpose of the invention is to offer novel nanoparticles which are useful in particular as contrast agents in imaging (e.g. MRI) and/or in other diagnostic techniques and/or as therapeutic agents, which give better performance than the known nanoparticles of the same type and which combine both a small size (for example less than 20 nm) and a high loading with metals (e.g. rare earths), in particular so as to have, in imaging (e.g. MRI), strong intensification and a correct response (increased relaxivity) at high frequencies. Thus, the nanoparticles according to the invention, with diameter $d_1$ between 1 and 20 nm, each comprise a polyorganosiloxane (POS) matrix including gadolinium cations optionally associated with doping cations; a chelating graft $C^1$ DTPABA (diethylenetriaminepentaacetic acid bisanhydride) bound to the POS matrix by an —Si—C— covalent bond, and present in sufficient quantity to be able to complex all the gadolinium cations; and optionally another functionalizing graft Gf\* bound to the POS matrix by an —Si—C— covalent bond (where Gf\* can be derived from a hydrophilic compound (PEG); from a compound having an active ingredient PA1; from a targeting compound; from a luminescent compound (fluorescein).
The method for the production of these nanoparticles and the applications thereof in imaging and in therapy also form part of the invention.

13 Claims, 17 Drawing Sheets

Related U.S. Application Data division of application No. 13/695,090, filed as application No. PCT/EP2011/056972 on May 2, 2011, now abandoned.

(51) Int. Cl.
| | |
|---|---|
| *A61K 41/00* | (2020.01) |
| *A61K 49/00* | (2006.01) |
| *B82Y 5/00* | (2011.01) |
| *B82Y 15/00* | (2011.01) |
| *A61K 9/00* | (2006.01) |

(52) U.S. Cl.
CPC ...... *A61K 49/0002* (2013.01); *A61K 49/0093* (2013.01); *A61K 49/1857* (2013.01); *A61K 49/1881* (2013.01); *A61K 9/0019* (2013.01); *B82Y 5/00* (2013.01); *B82Y 15/00* (2013.01); *Y10T 428/2982* (2015.01)

(56) References Cited

U.S. PATENT DOCUMENTS

| | | |
|---|---|---|
| 2009/0317335 A1 | 12/2009 | Lin et al. |
| 2011/0027375 A1 | 2/2011 | Tillement et al. |

FOREIGN PATENT DOCUMENTS

| | | |
|---|---|---|
| FR | 2930890 | 11/2009 |
| WO | WO 2005/061009 | 7/2005 |
| WO | WO 2007/124131 | 11/2007 |
| WO | WO 2009/142754 | 11/2009 |

OTHER PUBLICATIONS

Eisenwiener, et al., "A Convenient Synthesis of Novel Bifunctional Prochelators for Coupling to Bioactive Peptides for Radiometal Labelling," *Bioorg. Med. Chem.*, vol. 10, pp. 2133-2135, (2000).

Faure, et al., "Core/shell Nanoparticles for Multiple Biological Detection with Enhanced Sensitivity and Kinetics," *Nanotechnology*, vol. 19, No. 48, pp. 85608, (2008).

International Search Report dated Apr. 12, 2012, which issued during prosecution of International Application No. PCT/2011/056972.

Koole, et al., "Magnetic Quantum Dots for Multimodal Imaging," *Wiley Interdisciplinary Reviews—Nanomedicine and Nanobiotechnology*, vol. 1, No. 5, pp. 475-491, (2009).

Louis, et al., "Nanosized Hybrid Particles with Double Luminescence for Biological Labeling," *Chemistry of Materials*, vol. 17, No. 7, pp. 1673-1682, (2005).

Roux, et al., "Multifunctional Gadolinium Oxide Nanoparticles: Towards Image-guided Therapy," *Imaging in Medicine*, vol. 2, No. 2, pp. 211-233, (2010).

Söderlind, et al., "Colloidal Synthesis and Characterization of Ultrasmall Perovskite GdFeO3 Nanocrystals," *Nanotechnology*, vol. 19, No. 8, pp. 85608, (2008).

The definition of matrix from the American heritage dictionary, https://www.ahdictionary.com/word/search.html?q=matrix, accessed on Jan. 11, 2016.

Voisin, et al., "Use of Lanthanide-Grafted Inorganic Nanoparticles as Effective Contrast Agents for Cellular Uptake Imaging," *Bioconjugate Chem.*, vol. 18, No. 4, pp. 1053-1063, (2007).

Bazzi, R. et al., "Synthesis and properties of europium-based phosphors on the nanometer scale: $Eu_2O_3$, $Gd_2O_3$:Eu, and $Y_2O_3$:Eu," *Journal of Colloid and Interface Science*, 2004, 273(1):191-197 (Abstract Only) 1 page.

Bernhard et al., "DOTAGA-Anhydride: A Valuable Building Block for the Preparation of DOTA-Like Chelating Agents," *Chemistry*, 2012, 18(25):7834-7841 (Abstract Only) 1 page.

Mignot et al., "A Top-Down Synthesis Route to Ultrasmall Multifunctional Gd-Based Silica Nanoparticles for Theranostic Applications," *Chem. Eur. J.*, 2013, 19:6122-6136.

Ou, M. et al., "Delocalization of 4f Electrons in Gadolinium Oxide on the Nanometer Scale," *J. Phys. Chem. C*, 2009, 113, 10, 4038-4041 (Abstract Only) 1 page.

\* cited by examiner

ULTRAFINE NANOPARTICLES COMPRISING A FUNCTIONALIZED POLYORGANOSILOXANE MATRIX AND INCLUDING METAL COMPLEXES; METHOD FOR OBTAINING SAME AND USES THEREOF IN MEDICAL IMAGING AND/OR THERAPY

CROSS REFERENCED TO RELATED APPLICATIONS

This application is a continuation application of U.S. patent application Ser. No. 15/677,167, filed on Aug. 15, 2017, which is a divisional application of U.S. patent application Ser. No. 13/695,090, filed on Feb. 28, 2013, which is a § 371 National Stage Application of PCT/EP2011/056972 filed May 2, 2011, which claims priority from FR 1053389, filed Apr. 30, 2010.

BACKGROUND OF THE INVENTION

Field of the Invention

The invention relates to novel biocompatible hybrid nanoparticles of very small size, useful in particular for diagnostics and/or therapy.

The invention also relates to the method for the production thereof and applications thereof.

In the field of diagnostics, these may be probes for biological labelling endowed with magnetic, fluorescent or radioactive properties, contrast agents for magnetic resonance imaging (MRI), for imaging by SPECT (Single Photon Emission Computed Tomography) scintigraphy, for imaging by PET (Positron Emission Tomography) scintigraphy, for fluorescence imaging, for optical imaging, for X-ray scanner imaging or for multimodal imaging.

In the field of therapeutics, the uses envisaged are as radiosensitizing or radioactive agents for radiotherapy (e.g. curietherapy), for neutron therapy, agents for PDT (photodynamic therapy), agents for the vectorization of molecules with a therapeutic effect or cellular labelling agents.

In the two fields mentioned above, the nanoparticles in question can be targeting agents for therapeutic or diagnostic sites in vivo.

Description of Related Art

The requirements for nanoparticles applied to diagnostics and/or to therapy are, among others:
 a high concentration of active agents (for detection of a signal as contrast agent for diagnostics and/or for therapeutic action),
 good molecular rigidity, which is important for good vectorization and/or in MR imaging,
 very good colloidal stability in a biological medium, excellent biocompatibility,
 accessibility (i.e. ease of access to the zone of interest) and even better efficacy for therapeutic targeting, in particular with respect to tumours,
 good renal elimination in vivo,
 favourable and appropriate biodistribution in vivo (no retention of the nanoparticles by the organs or preferential retention in the targeted organs).

MRI is one of the most used techniques for medical diagnostics, combining the advantages of being non-invasive, quick and without danger for the patient. It is based on observation of the relaxation of the protons of water, which is directly dependent on magnetic fields (the important magnetic field $B_0$ and radio-frequency fields), pulse sequence, the environment of the water in the organism, etc. Interpretation of the images then gives access to identification of most tissues. The contrast can be increased by two types of agents: positive $T_1$ and negative $T_2$ contrast agents. In the context of the invention, we are interested in particular in these positive contrast agents, i.e. $T_1$, which permit lightening of the image as contact of water with the contrast agent makes it possible to reduce the longitudinal relaxation time: $T_1$. As examples of $T_1$ contrast agents used in clinical practice, there may be mentioned: Gd(III)DTPA or Gd(III)DOTA.

The $T_2$ contrast agents are those that make it possible to reduce the transverse relaxation time. Encapsulated superparamagnetic iron oxide nanoparticles are examples of $T_2$ agents used in clinical practice.

The $T_1$ contrast agents are preferable to the $T_2$ contrast agents, because of the positive contrast that they provide. Unfortunately, the non-specificity, the low contrast that they produce, their rapid renal excretion and their field-dependent properties further restrict their application. Moreover, the often low local concentration of gadolinium ions makes it difficult to detect medical abnormalities under a few centimetres in size. It would therefore be desirable to be able to apply specific targeting of sites in vivo, by means of gadolinium-laden elements. In this connection, nano-objects offer several advantages: higher local concentration of Gd and greater relaxivity ($r_1$) by gadolinium on account of the more consistent mass and rigidity of the nanoparticles.

In addition to improvement of the contrast, it is also desirable to limit the concentration of contrast agents in the human body.

All these aspects limit the usefulness of molecular compounds as contrast agents (the commercially available $T_1$ agents described above are indeed molecular agents, this is not the case for the $T_2$ agents but the latter are less interesting owing to the negative contrast that they provide).

A multimodal approach is adopted for these particles. This approach employs a set of nanoparticles comprising several molecular contrast agents. It makes it possible to combine not only different imaging techniques, but also different therapeutic techniques by combining several therapeutically active agents in one and the same set of nanoparticles. The active agents in imaging and the active agents in therapy may be identical or different.

This approach seems to be particularly suitable for the development of medicinal products in theranostics. In particular it is possible to add other imaging functions (luminescence, scintigraphy, etc.), therapeutic functions (release of active ingredients, radiosensitization, curietherapy, etc.) as well as functions of biological targeting for concentrating the therapeutic agents in the zone of interest.

Molecular compounds, because of their small size, do not generally allow combining several active agents, i.e. several properties within one and the same set (lack of space at the level of a molecular compound).

FR-2867180-B1 describes hybrid nanoparticle probes for biological labelling (fluorescence-luminescence-radioactivity), for detection (recognition) or the monitoring of specific substances, called targets. Such probes are used in particular for flow cytometry, histology, immunological assays or fluorescence microscopy, for the investigation both of biological materials and of non-biological materials. The nanoparticles according to FR-2867180-B1 have a core/shell structure, where the core is composed to at least 90% by weight of $Gd_2O_3$ i.e. a rare earth oxide optionally doped with a rare earth or an actinide, and where the shell is a coating consisting mainly of polysiloxane obtained by sol/gel hydrolysis/condensation of aminopropyltriethoxysilane (APTES) and of tetraethoxysilane (TEOS) in the presence of triethylamine. The diameter of this core/shell structure is for example 8.5, 11.5 or 9.2 nm. The polyorganosiloxane (POS) shell can be functionalized, i.e. grafted with a labelling dye (fluorescein) or a biological ligand such as a nucleic acid.

FR-2922106-A1 describes the use of radiosensitizing hybrid nanoparticles, with a high concentration of lanthanide oxides, as radiosensitizing agents that act in combination with radiation to induce a more effective response and increase the therapeutic efficiency. These nanoparticles have a core/shell structure in which the core (diameter e.g. 1.5 nm) is composed of $Gd_2O_3$ (optionally combined in 50/50 mixture with holmium oxide), and in which the shell is a coating consisting mainly of polysiloxane obtained by sol/gel hydrolysis/condensation of aminopropyltriethoxysilane (APTES) and of tetraethoxysilane (TEOS) in the presence of triethylamine. The diameter of this core/shell structure is for example 2.7 nm. The POS shell is then functionalized, i.e. grafted either with a polyol such as polyethylene glycol, or with a chelating agent, e.g. diethylenetriamine pentaacetic acid (DTPA). This type of functionalized core/shell nanoparticle has for example a total diameter of 11.7 nm.

FR-2930890-A1 discloses novel agents for targeted radiotherapy or for curietherapy (with radionuclides) consisting of nanoparticles with a high concentration of oxide or oxohydroxide of radioactive rare earths. These nanoparticles are for example nanoparticles consisting of a core of holmium oxide coated with functionalized polysiloxane. The core is obtained by dissolving holmium chloride salts in diethylene glycol. The size of this core is about 1.5 nm. The layer of functionalized polysiloxane with a thickness of 0.5 nm is synthesized by a sol-gel process, mainly starting from APTES and TEOS. The particles thus coated are then functionalized either with PEG250, or with dianhydrous diethylenetriaminepentaacetic acid (DTPABA). The suspension thus prepared is lyophilized The hydrodynamic sizes are, for the core: 1.5 nm; after coating: 3.1 nm and after functionalization with DTPABA: 3.6 nm; after lyophilization: 4.0 nm.

The nanoparticles according to these three documents FR-2867180-B1, FR-2922106-A1 and FR-2930890-A1 are in particular interesting for their polysiloxane shell, which improves their biocompatibility. Their small size is a further plus with regard to renal elimination (clearance) and biodistribution in vivo. However, the element acting as T1 contrast agent in MRI in these nanoparticles, namely for example gadolinium present at the centre of the core of lanthanide oxide, is far less accessible to water than that on the surface or than that which would be complexed with DTPA or DOTA within or on the surface of the layer of polysiloxane. This leads to a lower efficacy of the object per atom of gadolinium for these nanoparticles of the core/shell type. Moreover, although it is possible to reach diameters of less than 10 nm for these nanoparticles with a core of gadolinium oxide, for example, this is achieved by reducing the size of the external layer of polysiloxane. This may result in problems of dissolution of the core connected with the reduced protection provided by a thinner layer of polysiloxane. This leads to risks of toxicity connected with the high local concentrations of gadolinium.

WO-2007124131-A discloses hybrid nanoparticles useful as multimodal contrast agents in imaging, in particular MRI. These hybrid nanoparticles comprise an inorganic polymer matrix based on silica (or organic: polyacrylate-polylactide) and a plurality of coordination complexes each having a functionalized chelating group (DTTA-DTPA-DOTA), a paramagnetic metal ion (lanthanide/actinide: Gd—Mn), a luminophore (fluorescein). The functionalizing radical is for example an aminopropyl-(trimethoxysilyl).

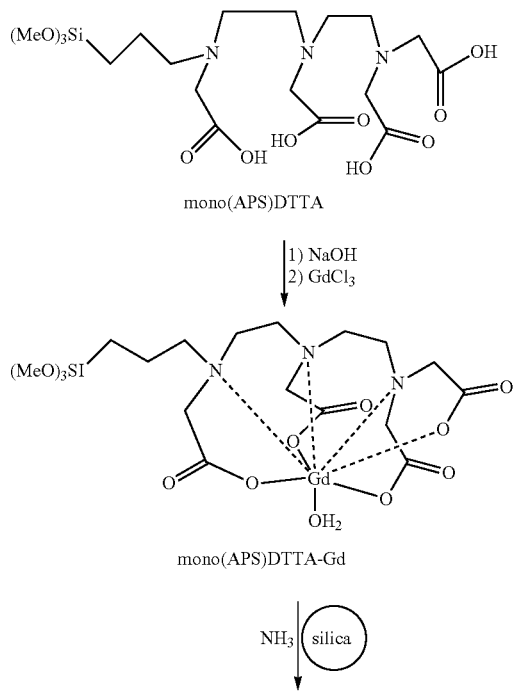

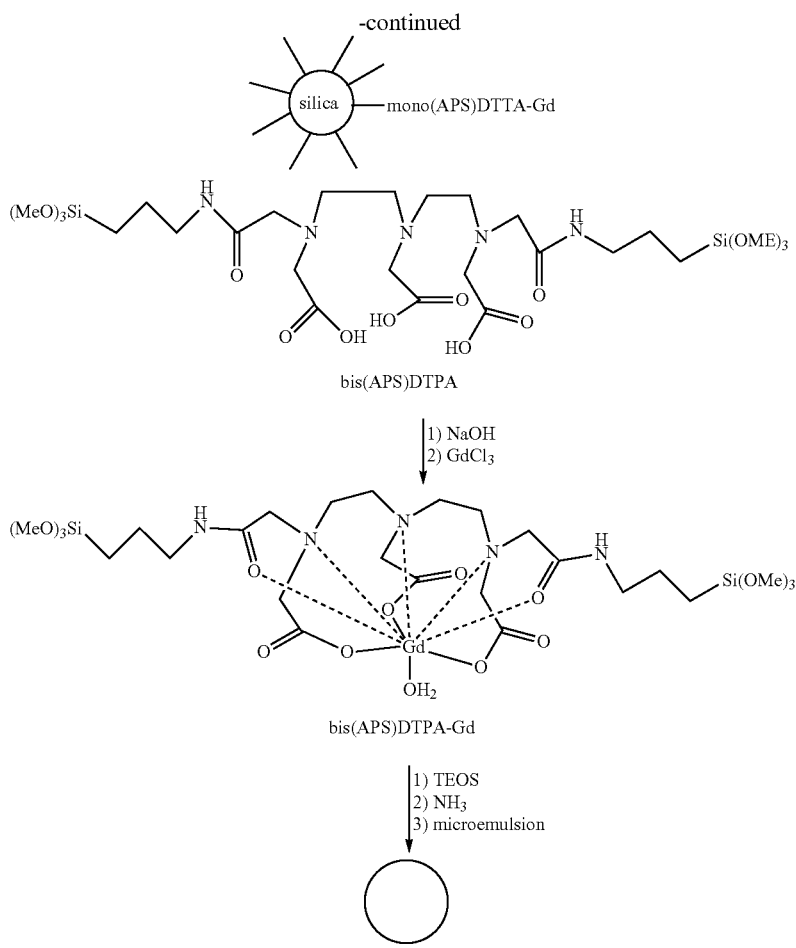

The silica nanoparticles thus obtained have a diameter of the order of 40 nm. These nanoparticles do not have a core/shell structure and therefore, a priori, do not have the associated drawbacks. However, their size of several tens of nanometres is a serious handicap in terms of elimination in vivo.

The prior art does not disclose nanoparticles combining a very small size, for example less than 20 nm, and a high level of loading with contrast agent, e.g. Ti for MRI (gadolinium). The very small size of the nanoparticles is essential for obtaining, in vivo, good renal elimination and suitable biodistribution.

The high loading with magnetic complexes combined with the size and the rigidity of the object makes it possible to obtain a high $r_1$ per object and per gadolinium atom (greater than that of the free ion and a fortiori of the molecular compounds), which is required in order to have, in imaging (e.g. MRI), a strong intensification and a correct response to high frequencies.

SUMMARY

The present invention aims to satisfy at least one of the following objectives:
(i) to offer novel nanoparticles that are useful in particular as contrast agents in imaging (e.g. MRI) and/or in other diagnostic techniques and/or as therapeutic agents, and which give better performance than the known nanoparticles of the same type;
(ii) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which combine at the same time a small size (for example under 20 nm) and a high loading with metals (e.g. rare earths), in particular in order to have, in imaging (e.g. MRI), a strong intensification (associated for example with a high relaxivity $r_1$) and a correct response (increased relaxivity) at high frequencies;
(iii) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which have a good molecular rigidity, which is important in MR imaging;
(iv) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which have excellent biocompatibility;
(v) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which have very good colloidal stability in biological media;

(vi) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which have an accessibility (the small particle size allows them to reach the zones of interest more easily) and even better efficacy for therapeutic targeting, in particular with respect to tumours;

(vii) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which have a high concentration of active ingredients;

(viii) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which show, in vivo, good renal elimination (clearance) and a favourable and appropriate biodistribution;

(ix) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and which are usable as a platform for combining many functionalities (in addition to those in MRI): imaging functions (fluorescence, scintigraphy, etc.) or therapeutic functions (radiosensitization, curietherapy, photodynamic therapy, etc.);

(x) to offer novel nanoparticles based on silicic polymer, metals (e.g. rare earths) and chelating agents, which are useful in particular as contrast agents in imaging (e.g. MRI) and/or in other diagnostic techniques and/or as therapeutic agents, and the toxicity of which associated with the metals (e.g. rare earths) that they contain is reduced;

(xi) to offer a novel method for the production of nanoparticles such as those referred to in objectives (i) to (x) above;

(xii) to offer novel suspensions of nanoparticles such as those referred to in objectives (i) to (x) above;

(xiii) to offer novel compositions for diagnostics, for contrast in imaging (e.g. MRI), for therapy or for cellular labelling, based on nanoparticles such as those referred to in objectives (i) to (x) above.

These objectives, among others, are achieved by the present invention, which in a first of its aspects relates to nanoparticles characterized (i) in that they each comprise a polyorganosiloxane (POS) matrix including cations (e.g. metal cations) $M^{n+}$ (n=2 to 6) preferably of a rare earth, optionally partly in the form of a metal oxide and/or oxohydroxide (M), optionally associated with doping cations $D^{m+}$ (m=2 to 6), preferably a rare earth different from M, an actinide and/or a transition element;

a chelating functionalizing graft $C^1$ which is:
 derived from a chelating agent C1,
 bound to the POS matrix by an —Si—C— covalent bond,
 and in sufficient quantity to be able to complex all the cations $M^{n+}$ and $D^{m+}$; the graft $C^1$ preferably being in excess relative to the cations $M^{n+}$ and $D^{m+}$; the chelating agent C1 from which the graft $C^1$ is derived corresponding to one or more different species;

optionally another functionalizing graft Gf* bound to the POS matrix by an —Si—C— covalent bond, where Gf* can be derived from:
 a hydrophilic compound (PEG),
 a compound having an active ingredient PA1,
 a targeting compound,
 a luminescent compound (e.g. fluorescein);

(ii) in that their diameter $d_1$ is comprised between 1 and 20 nm, preferably between 1 and 10 nm;

(iii) and optionally in that they bear an active ingredient PA2, identical to or different from PA1.

In a second aspect, the invention relates to a method for the production of nanoparticles according to at least one of the preceding claims, characterized in that it comprises the following steps:

a Synthesis of cores based on a metal oxide and/or oxohydroxide (M), preferably of a rare earth, at least partly in cationic form $M^{n+}$ (n=2 to 6), optionally doped with a dopant (D), preferably a rare earth different from M, an actinide and/or a transition element;
 this synthesis consisting essentially of mixing a base (preferably a strong base such as NaOH) with a salt of M dissolved in a solvent preferably selected from the group comprising alcohols (advantageously DEG);

b Coating of the cores from step (a) with polyorganosiloxane (POS) consisting essentially of employing a sol/gel technique for hydrolysis-condensation of silicic species and alkoxysilanes, in the presence of a base or of an acid and optionally of an active ingredient PA1 and/or PA2;

c Functionalizing overcoating of the coated cores from step (b) consisting essentially of bringing said coated cores from step (b) into contact with a precursor of functionalizing grafts $C^1$ (preferably derived from a chelating agent C1 selected from the products defined below), and optionally into contact with a functionalizing graft Gf* (preferably a hydrophilic compound and/or a compound having an active ingredient PA1 and/or a biological targeting compound and/or a luminescent compound selected from the products defined below);

d Purification of the overcoated/functionalized nanoparticles of diameter $d_0$, preferably by tangential filtration, dialysis and/or by precipitation/washing;

e Dissolution of the cores M of the overcoated/functionalized nanoparticles from step (c) consisting essentially of bringing them into contact with a pH modifier and/or a chelating agent C2 that is able to complex some or all of the cations $M^{n+}$ and $D^{m+}$, so that the diameter $d_0$ of the nanoparticles is reduced to a value $d_1$ comprised between 1 and 20 nm, preferably between 1 and 10 nm; said chelating agent C2 being selected from the chelating products defined below;

f Optional addition of a cationic salt intended to be at least partly complexed by the chelating agent $C^1$;

where steps (c), (d), (e), (f) can be carried out in a different order or at the same time. In the case when the whole core is dissolved in step (c), step (e) becomes optional.

In a third aspect, the invention relates to a suspension of nanoparticles and the dry extract of said suspension.

In a fourth aspect, the invention relates to an injectable liquid comprising these nanoparticles.

In a fifth aspect, the invention relates to:
 a composition as a diagnostic aid, preferably a contrast composition,
 a therapeutic composition,
 or a cellular labelling composition,
characterized in that it comprises nanoparticles according to the invention and/or obtained by the method according to the invention and/or from the suspension according to the invention and/or prepared from the solid material according to the invention.

Definitions

Throughout this text, singular denotes indiscriminately singular or plural. The definitions of the terms used in the context of the present disclosure and presented below, correspond to terminology according to the invention and are only given non-limitatively.

APTES denotes (3-aminopropyl)triethoxysilane.

BAPTA denotes 1,2-bis-2-aminophenoxyethane-N,N,N', N'-tetraacetic acid.

DEG denotes diethylene glycol.

DOTA denotes 1,4,7,10-tetraazacyclododecane-1,4,7,10-tetraacetic acid.

DOTA-NHS denotes 1,4,7,10-tetraazacyclododecane-1,4, 7,10-tetraacetic acid N-hydroxysuccinimide DTPA denotes diethylenetriaminepentaacetic acid.

DTPABA denotes diethylenetriaminepentaacetic acid bisanhydride.

DTTA denotes diethylenetriaminetetraacetic acid.

EDTA denotes ethylenediaminetetraacetic acid.

EGTA denotes ethylene glycol acid-bis(2-aminoethylether)-N,N,N',N'-tetraacetic acid EXAFS denotes: "Extended X-Ray Absorption Fine Structure".

MRI denotes: "Magnetic Resonance Imaging".

NOTA denotes 1,4,7-triazacyclononane-N,N',N''-triacetic acid.

PDT denotes: "photodynamic therapy"

PET denotes: "Positron Emission Tomography" or PET scintigraphy.

PEG denotes polyethylene glycol.

POS denotes polyorganosiloxane.

PPG denotes polypropylene glycol.

SPECT denotes: "Single Photon Emission Computed Tomography" or SPECT scintigraphy TEOS denotes tetraethoxysilane.

TEM denotes transmission electron microscopy.

XPS denotes: "X-ray photoelectron spectroscopy".

A "hydrophilic" compound denotes a compound having a strong affinity for water, "strong" means for example a compound that can be dissolved or dispersed homogeneously in water at room temperature at more than 100 grams per litre of solution.

"alkyl" denotes a saturated, linear or branched hydrocarbon chain, optionally substituted (e.g. with one or more alkyls), preferably with 1 to 10 carbon atoms, for example with 1 to 8 carbon atoms, better still with 1 to 7 carbon atoms.

Examples of alkyl groups are in particular methyl, ethyl, isopropyl, n-propyl, tert-butyl, isobutyl, n-butyl, n-pentyl, isoamyl and 1,1-dimethylpropyl.

The alkyl moiety of the alkoxy group is as defined above.

"cycloalkyl" denotes a saturated mono- or polycyclic, preferably mono- or bicyclic, hydrocarbon group preferably having from 3 to 10 carbon atoms, more preferably from 3 to 8.

"saturated polycyclic hydrocarbon group" denotes a group having two or more cyclic nuclei attached to one another by π bonds and/or condensed two by two.

Examples of polycyclic cycloalkyl groups are adamantane and norbornane.

Examples of monocyclic cycloalkyl groups are cyclopropyl, cyclobutyl, cyclopentyl, cyclohexyl, cycloheptyl and cyclooctyl.

"aryl" denotes an aromatic hydrocarbon group, having from 6 to 18 carbon atoms, monocyclic or polycyclic and preferably monocyclic or bicyclic. It must be understood that, in the context of the invention, "polycyclic aromatic group" means a group having two or more aromatic nuclei, condensed (orthocondensed or ortho and pericondensed) with one another, i.e. having, two by two, at least two carbons in common.

Said aromatic hydrocarbon group ("aryl") is optionally substituted for example with one or more C1-C3 alkyls, one or more halogenated hydrocarbon groups (e.g. $CF_3$), one or more alkoxy (e.g. $CH_3O$) or one or more hydrocarbon groups comprising one or more ketone units (e.g. $CH_3CO-$).

As examples of aryl, there may be mentioned the phenyl, naphthyl, anthryl and phenanthryl, phenyl; p-chlorophenyl; m-chlorophenyl; dichloro-3,5-phenyl; trichlorophenyl; tetrachlorophenyl; o-, p- or m-tolyl; α,α,α-trifluorotolyl; xylyls such as dimethyl-2,3-phenyl; dimethyl-3,4-phenyl radicals.

These groups can optionally be halogenated, or alternatively can be selected from the cyanoalkyl radicals.

The halogens are for example fluorine, chlorine, bromine and iodine, preferably chlorine or fluorine.

"aralkyl" denotes an alkyl group as defined above, substituted with one or more aryl groups on its hydrocarbon chain, the aryl group being as defined above. Examples of this are benzyl and triphenylmethyl.

"alkenyl" denotes an unsaturated, linear or branched, substituted or unsubstituted hydrocarbon chain, having at least one olefinic double bond, and more preferably a single double bond. Preferably, the "alkenyl" group has from 2 to 8 carbon atoms, more preferably from 2 to 6. This hydrocarbon chain optionally comprises at least one heteroatom such as O, N, S.

Preferred examples of alkenyl groups are the vinyl, allyl and homoallyl groups.

"alkynyl" denotes, according to the invention, an unsaturated, linear or branched, substituted or unsubstituted hydrocarbon chain, having at least one acetylene triple bond, and more preferably a single triple bond. Preferably, the alkynyl group has from 2 to 8 carbon atoms, more preferably from 2 to 6 carbon atoms. As examples, there may be mentioned the acetylenyl group, as well as the propargyl group. This hydrocarbon chain optionally comprises at least one heteroatom such as O, N, S.

DETAILED DESCRIPTION OF A PREFERRED EMBODIMENT

Nanoparticles of the Invention

The nanoparticles according to the invention can be defined by their POS matrix structure including a chelating functionalization $C^1$ derived from a chelating agent C1 and leading to the formation of complexes $[M^{n+}]/[C^1]$ or even $[D^{m+}]/[C^1]$, and, according to an optional but nevertheless preferred embodiment, functionalizing grafts Gf* for example derived from:

a hydrophilic compound (PEG);

a compound having an active ingredient PA1;

a targeting compound;

and/or a luminescent compound (fluorescein).

The nanoparticles according to the invention can also be defined by their method for the production. The nanoparticles thus defined constitute in themselves another subject of the invention and are characterized in that the POS matrix of each nanoparticle is obtained from a nanoparticle of diameter $d_0$ comprising:

a core based on a metal oxide and/or oxohydroxide (M), preferably of a rare earth, at least partly in cationic form $M^{n+}$ (n=2 to 6), optionally doped with a dopant (D), preferably a rare earth different from M, an actinide and/or a transition element;

at least one coating layer based on POS;

and optionally overcoating based on a functionalizing agent, preferably selected from functionalizing chelating agents C1 that are able to sequester cations and/or targeting compounds and/or compounds having an active ingredient PA1 and/or hydrophilic compounds and/or luminescent compounds;

said nanoparticle being subjected to dissolution of the core M, preferably by means of a pH modifier and/or of a chelating agent C2, identical to or different from C1, that is able to complex some or all of the cations $M^{n+}$ and $D^{m+}$, so that the diameter $d_0$ of the nanoparticle is reduced to a value $d_1$ comprised between 1 and 20 nm, preferably between 1 and 10 nm.

These nanoparticles therefore have the particular feature of being "coreless", or more precisely of no longer having a core. They do not comprise a crystallized core. Even more precisely, they do not comprise a core encapsulated by at least one coating.

Figure 1:
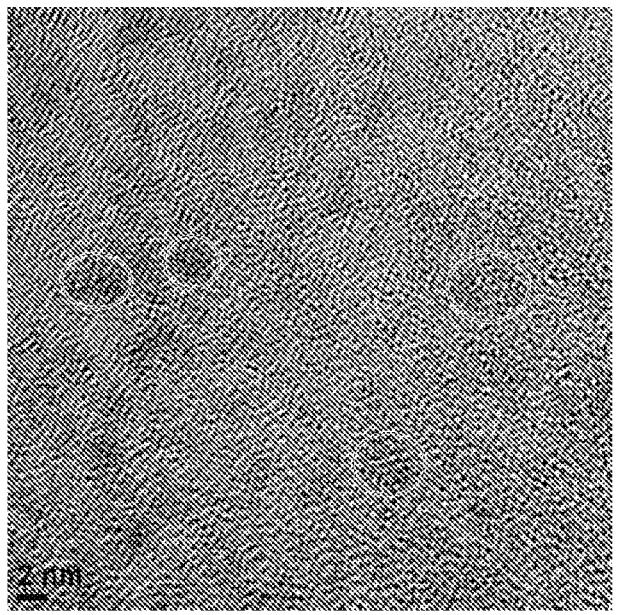
FIGS. 1-32 represent embodiments as described therein.
Figure 2:
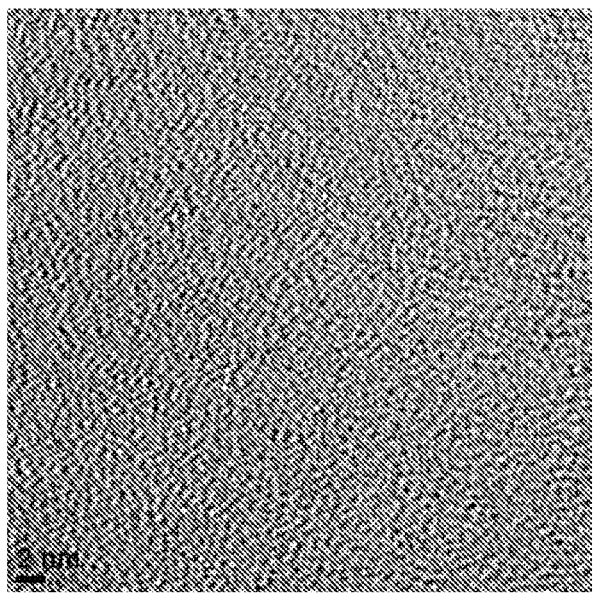

In order to illustrate this, reference may be made non-limitatively to the attached FIGS. 1 and 2. FIG. 1 is a TEM image (microscope magnification ×600 000) of precursor particles of the nanoparticles according to the invention. These precursor particles are formed by cores of metal oxide M (gadolinium oxide), coated with polysiloxane, and functionalized by a complexing agent $C^1$ (e.g. DOTAGA anhydride). The sizes observed are comprised between 3 and 5 nm.

The molecules of DOTA are not visible with TEM, only the coated core is seen. The attached FIG. 2 is a TEM image after dissolution of the cores, taken under the same conditions as the image in FIG. 1. No particle is observed that would comprise a core, whereas local chemical analysis indicates the presence of gadolinium in the zone observed.

An essential feature of these ultrafine particles is due to their very small size, of the order of some nanometres. At these very small sizes (less than or equal to, in increasing order of preference, 20; 18; 15; 12; 10; 8; 5; 3 nanometres), the particles display quasi-molecular behaviour, permitting:

very good colloidal stability in biological media, a favourable biodistribution with the possibility of elimination by appropriate natural routes, i.e. renal biodistribution without capture in vital organs, while having a longer retention time than that of molecular complexes, and moreover the fact that they are more massive means that diffusion is not significant, better accessibility and efficacy for tumour targeting, possibility of inserting a high concentration of active elements, i.e. of obtaining a high level of chelating agents C1 grafted on and within the polysiloxane matrix and of obtaining a high ratio of C1 to silicon, advantageously greater than or equal to, in increasing order of preference, 1; 5; 10; 20; 30; 40; 50% by weight. For finding a given signal or a therapeutic effect associated with the complexed element, this then limits injection of the exogenous element silicon.

Regarding their size, it can be observed that these nanoparticles are also characterized by their molecular weight (in kDa) greater than or equal to, in increasing order of preference, 2, 3, 5, and less than or equal to, in increasing order of preference, 200, 100, 50, 20, 10.

Their very good chemical stability and compatibility are two very important characteristics of these nanoparticles. Their basic skeleton is formed of POS, i.e. predominantly compounds comprising Si, C, H, O and N, the basis of silicones, compounds that are renowned for their very good biocompatibility and their low toxicity. The additional active elements, such as metal cations are for their part inserted in the particles by complexing using molecules that are stable and recognized as reliable for biological applications. The residual concentration of free ions can then be controlled and kept well below the critical toxicity thresholds. The exchanges of complexed cations with endogenous cations can also be controlled by using a proportion of the chelating functions $C^1$ within one and the same particle. The possibility of adding, on the nanoparticles, complexing agents that are free (e.g. C2) from metal cations ensures that accidental release of M (e.g. of gadolinium) or even of D, can be compensated for immediately by complexing with another chelating agent, thus reducing the risks of toxicity connected with the nature of gadolinium.

These "coreless" POS nanoparticles comprise a high density of chelating grafts $C^1$ bound (or not C2) covalently to the POS skeleton (matrix).

Preferably, the chelating agents C1 and/or C2 are present in the nanoparticles in a quantity such that some or all of the ions, in particular the cations $M^{n+}$ or $D^{m+}$ are not free but are complexed. More preferably, the percentage by weight of the elements M and D involved in M-O-M or M-O-D or D-O-D or M-O—Si or D-O—Si bonds, relative to the total number of elements M and D, is less than or equal to, in increasing order of preference 10; 5; 2, 1; 0.5; $10^{-1}$; $10^{-2}$; $10^{-3}$.

The number of chelating agents $C^1$ and/or C2 in the nanoparticles is greater than the number of remaining cations $M^{n+}$ and/or $D^{m+}$, or even of other cations (e.g. $Ca^{++}$, $Mg^+$) optionally added in addition to $M^{n+}$ and/or $D^{m+}$.

This percentage of M-O-M or M-O-D or D-O-D or M-O—Si or D-O—Si bonds (oxides) can be measured by known techniques such as EXAFS, XPS, vibrational spectroscopy, transmission electron microscopy coupled to structural analyses etc.

Based on this measurement, the number of specific bonds of the core can be evaluated, the presence or absence of the core can be measured quantitatively, and it is possible to evaluate the species M or D that could easily dissolve and be present in ionic form in solution.

The chelating agents C1 can be surface-grafted on the polysiloxane particles or inserted directly into the POS matrix. Some or all of these chelating agents are intended for complexing cations $M^{n+}$ (e.g. of gadolinium) or even $D^{m+}$. Another proportion of these chelating agents can serve for complexing endogenous cations to ensure good compatibility with the biological media encountered.

Preferably, at least 1% and preferably at least 10% of the chelating agents $C^1$ are not complexed by cations $M^{n+}$, nor even $D^{m+}$.

One of the major benefits of the nanoparticles according to the invention is that M and/or D can be an active agent in imaging (e.g. a contrast agent) and/or in therapy.

In fact, $M/M^{n+}$ (e.g. of gadolinium) or even $D/D^{m+}$ display remarkable properties for biological applications in imaging and/or in therapy, for example magnetic, fluorescent, radioactive (element of high atomic number) or radiosensitizing (X, gamma, beta, neutron) properties.

These nanoparticles can therefore be used as contrast agents in imaging systems such as: MRI, SPECT scintigraphy, PET scintigraphy, fluorescence imaging, X-ray scanners.

Besides chelating functionalization $C^1$, these nanoparticles can be surface-modified (functionalization) by hydrophilic compounds (PEG) and/or charged differently to adapt their biodistribution within the body and/or permit good cellular labelling, in particular for monitoring cellular therapies.

Moreover, they can be surface-functionalized by biological targeting compounds, for preferential access to certain zones of interest in the body, particularly zones with tumours. In this way the agent carried by these nanoparticles is concentrated in the zone of interest without requiring a large increase in the quantities injected, as is currently the case.

Functionalization can also be effected with compounds comprising an active ingredient PA1 and/or luminescent compounds (fluorescein).

This results in possible therapeutic uses as radiosensitizing agents in combination with radiotherapies, neutron therapies, as radioactive agents for treatments in curietherapy, as agents for PDT (photodynamic therapy) or as agents for vectorization of molecules with a therapeutic effect.

An essential feature of these ultrafine particles arises from their very small size, of the order of a few nanometres. At these very small sizes (less than or equal to, in increasing order of preference, 20; 18; 15; 12; 10; 8; 5; 3 nanometres), the particles display quasi-molecular behaviour, permitting:
  very good colloidal stability in biological media,
  a favourable biodistribution with a possibility of elimination by the appropriate natural routes, i.e. renal biodistribution without capture in the vital organs, while having a longer retention time than that of molecular complexes, and moreover the fact that they are more massive means that diffusion is not significant,
  better accessibility and efficacy for tumour targeting,
  possibility of inserting a high concentration of active elements, i.e. to obtain a high level of chelating agents C1 grafted on and within the polysiloxane matrix and obtain a high ratio of C1 to silicon, advantageously greater than or equal to, in increasing order of preference, 1; 5; 10; 20; 30; 40; 50% by weight. For finding a given signal or a therapeutic effect associated with the complexed element, this then limits injection of the exogenous element silicon.

Regarding size, it can be observed that these nanoparticles are also characterized by their molecular weight (in kDa) greater than or equal to, in increasing order of preference, 2, 3, 5, and less than or equal to, in increasing order of preference, 200, 100, 50, 20, 10.

Their very good chemical stability and compatibility are two very important characteristics of these nanoparticles. Their basic skeleton is formed of POS, i.e. predominantly of compounds comprising Si, C, H, O and N, the basis of silicones, compounds renowned for their very good biocompatibility and their low toxicity. The additional active elements, such as metal cations, for their part are inserted in the particles by complexing using molecules that are stable and recognized as reliable for biological applications. The residual concentration of free ions can then be controlled and kept well below the critical toxicity thresholds. The exchanges of complexed cations with endogenous cations can also be controlled by using a proportion of the chelating agents C1 within one and the same particle. The possibility of adding, on the nanoparticles, complexing agents that are free from metal cations ensures that accidental release of M (e.g. of gadolinium) or even of D can be compensated for immediately by complexing with another chelating agent, thus reducing the risks of toxicity connected with the nature of gadolinium.

Another feature of these nanoparticles is maintenance of the rigid character of the objects and of the overall geometry of the particles after injection. This high three-dimensional rigidity is provided by the polysiloxane matrix, where the majority of the silicons are bound to 3 or 4 other silicon atoms via an oxygen bridge. The combination of this rigidity with their small size makes it possible to increase the relaxivity of these nanoparticles for the intermediate frequencies (20 to 60 MHz) relative to the commercially available compounds (complexes based on Gd-DOTA for example), but also for frequencies above 100 MHz present in the new generation of high-field MRI systems.

This rigidity, which is not present in the polymers, is a further advantage for the vectorization and accessibility of the targeting molecules.

Moreover, it must be emphasized that the biocompatibility of these nanoparticles is not the least of their qualities.

General Formula

The nanoparticles according to the invention are also characterized by the following general formula:

$$[C^1]_a[R]_b\text{Si}[O]_c[OH]_d[M^{n+}]_e[D^{m+}]_f[Gf^*]_g$$

where:
  $C^1$ are chelating functionalizing grafts formed by monovalent hydrocarbon radicals, identical to or different from one another, and each connected to the Si by an Si—C bond;
  R are monovalent radicals, identical to or different from one another, constituting a functionalizing graft connected to the Si by an Si—C bond, and preferably comprising a hydrophilic group and at least one N or O atom;
  $M^{n+}$ are metal cations, identical to or different from one another, with n=2 to 6;
  $D^{m+}$ are metal cations, identical to or different from one another, with m=2 to 6;
  $Gf^*$ are functionalizing grafts other than $C^1$, formed by monovalent hydrocarbon radicals, identical to or different from one another, each connected to the Si by an Si—C bond, and which can be derived from:
    a hydrophilic compound (PEG);
    a compound having an active ingredient PA1;
    a targeting compound;
    a luminescent compound (fluorescein);
  a greater than or equal to 0.01 and less than or equal to 0.8; preferably with a≥d+e;
  b less than or equal to 0.7;
  c greater than or equal to 0.5 and less than 1.9;
  g greater than or equal to 0 and less than 0.3;
  e+f greater than or equal to 0.01 and less than or equal to 0.8;
  e+f less than or equal to a;
  a+b+2c+d+g=4;
  a+b+g comprised between 0.25 and 0.95.

The monovalent hydrocarbon radicals are e.g. alkyls, cycloalkyls, aryls, aralkyls, alkenyls or alkynyls.

The Quantity of Silicon in the POS Matrix Relative to the Other Constituents

The atomic ratio [(M/Si)*100] is another representative parameter of the nanoparticles according to the invention. Thus, these nanoparticles are characterized by an atom-% ratio [(M/Si)×100] comprised between 10 and 60, preferably between 25 and 40.

According to another remarkable feature of the invention, 1 to 80%, and preferably 20 to 60%, of the silicons of the POS matrix of the nanoparticles are bound, by a silane bond Si—C, to at least one chelating agent C1.

In other words, 25 to 95% and preferably from 40 to 60% of the silicon atoms of the POS matrix are bound covalently to a carbon atom.

Advantageously, at least 20; 25; 30; 35; 40; 45; 50; 60%, in increasing order of preference, of the silicons of the POS matrix of the nanoparticles are bound, by a silane bond Si—C, to at least one chelating functionalizing group $C^1$, and/or to at least one other functionalizing graft Gf* bound to the POS matrix by an —Si—C— covalent bond, where Gf* can be derived from:
- a hydrophilic compound (PEG);
- a compound having an active ingredient PA1;
- a targeting compound;
- a luminescent compound (fluorescein).

In a preferred embodiment in which each of the nanoparticles comprises at least one outer layer comprising a chelating functionalizing graft $C^1$ surface-grafted on the POS matrix, it is envisaged that between 1 and 80%, ideally 20 and 60% of the silicon atoms are bound by Si—C bonds to the chelating functionalizing graft $C^1$.

Multimodality

Advantageously, these nanoparticles can be produced to have a multimodality of properties, i.e. they are multimodal, in particular on account of the various cations $M^{n+}$, or even $D^{m+}$ that they comprise, which are complexed by $C^1$, and which can be used as contrast agent(s) in imaging and/or as therapeutic agent(s). For example, same nanoparticles display:
- behaviour as a contrast agent for at least two of the detection techniques, for example MRI and scintigraphy or MRI and fluorescence,
- or two different behaviours as a therapeutic agent,
- or at least one behaviour as a contrast agent and at least one behaviour as a therapeutic agent.

These novel nanoparticles can therefore be used as a platform making it possible to combine many functionalities (in addition to those in MRI): imaging functions (fluorescence, scintigraphy, etc.) and/or therapeutic functions (radiosensitization, curietherapy, photodynamic therapy, etc.).

Relaxivity

Preferably, the nanoparticles according to the invention have a relaxivity $r_1$ per $M^{n+}$ ion greater than 5 $mM^{-1}$ (of ion)·$s^{-1}$ preferably 10 $mM^{-1}$ (of $M^{n+}$ ion)·$s^{-1}$ for a frequency of 20 MHz.

More preferably, these nanoparticles have a relaxivity $r_1$ per $M^{n+}$ ion at 60 MHz that is greater than or equal to the relaxivity $r_1$ per $M^{n+}$ ion at 20 MHz.

The relaxivity $r_1$ considered here is a relaxivity per $M^{n+}$ ion (for example gadolinium). $r_1$ is found from the following formula: $1/T_1 = [1/T_1]_{water} + r_1[M^{n+}]$ Metallic Active Elements (Cations) M and Dopants D Preferably, M and D are selected from the following groups of elements: lanthanides, transition elements, actinides, elements of columns Ib, IIa, Ma, IIIb, Va, VIb, VIIb, VIII of the periodic table according to "The Merck Index—Eleventh edition";
preferably from the subgroups comprising:
- the following lanthanides: Gd, Dy, Eu, Tb, Nd, Yb, Er, Ho, Lu;
- Ib: Cu, Ag, Au;
- IIa: Ca, Mg;
- IIIa: Ga, In;
- IIIb: Y;
- Va: Bi;
- VIb: Cr, Mo;
- VIIb: Mn, Tc;
- VIII: Fe, Ru, Pt, Rh, Ir.

Gd, Dy are very suitable e.g. for nanoparticles useful as contrast agents in MRI.

Eu, Tb, Nd, Yb, Er are very suitable e.g. for nanoparticles useful as fluorescence agents.

Ho, Lu are very suitable e.g. for nanoparticles useful as agents in curietherapy.

Lu, Yb, Gd, Ho are very suitable e.g. for nanoparticles useful as radiosensitizing agents.

Location of the Metallic Active Elements (Cations) M and Dopants D

According to an advantageous feature of the invention, the cations Mn+ and/or Dm+ are located on the surface of the nanoparticles.

Hence it follows that these cations are close to water molecules and can thus in particular have an important effect of enhancing contrast $T_1$ in MRI. This improvement in the performance of the nanoparticles according to the invention is one indication, among others, of the location of the cations $M^{n+}$ and/or $D^{m+}$ on the surface.

Chelating Agents C1, C2 or C3

Advantageously, the chelating agent C1, C2 is selected from the following products:
- products in the group of polyaminated polycarboxylic acids and derivatives thereof, and even more preferably from the subgroup comprising: DOTA, DTPA, EDTA, EGTA, BAPTA, NOTA and mixtures thereof;
- products in the group comprising porphyrin, chlorine, 1,10-phenanthroline, bipyridine, terpyridine, cyclam, triazacyclononane, derivatives thereof and mixtures thereof;
- and mixtures thereof.

As examples of chelating agents, there may be mentioned those comprising a DTPA, DOTA, DTDTPA (dithiolated DTPA) unit or a succinic acid unit.

If M is a lanthanide, C1, C2 is advantageously selected from those that have lanthanide complexing properties, in particular those whose complexation constant $\log(K_{C1})$ is above 15, preferably 20 (e.g. DTPA or DOTA).

Hydrophilic Compounds

According to a preferred embodiment of the invention, the hydrophilic compounds from which the functionalizing grafts are derived are selected from the group of polyols, preferably from the subgroup comprising glycols, sugars and mixtures thereof; the dextrans, PEG and PPG being particularly preferred.

According to an alternative embodiment, these hydrophilic compounds can be selected from those that have molecular weights below 2000 g/mol, preferably below 800 g/mol. Some examples of hydrophilic compounds are given below, with their preferred molecular weight (Mw):
- Poly(ethyleneglycol)bis(carboxymethyl)ether (PEG), 250<Mw<2000 g·$mol^{-1}$;
- Polyoxyethylene bis(amine), 250<Mw<2000 g·$mol^{-1}$;
- O-Methyl-O'-succinylpolyethylene glycol, Mw of the order of 2000 g·$mol^{-1}$;
- Methoxypolyethylene glycolamine Mw of the order of 750 g·$mol^{-1}$;

Succinic and mercaptosuccinic acid;

Sugars, in particular glucose and its derivatives, for example dextrans;

Hydrophilic amino acids or peptides (aspartic acid, glutamic acid, lysine, cysteine, serine, threonine, glycine, etc.);

and mixtures thereof.

More generally, the hydrophilic compounds advantageously comprise alcohol or carboxylic acid functions or amines or amides or esters or ether-oxides or sulphonates or phosphonates or phosphinates and will be bound, preferably covalently, to at least 10% of the silicon atoms of the POS of the matrix.

It goes without saying that the chelating agent C1, C2 can be a hydrophilic compound and vice versa.

The Active Ingredient PA1 or PA2 Different from [$M^{n+}$]/[C1] and [$D^{m+}$]/[C1], According to a useful embodiment of the invention, the nanoparticles carry an active ingredient PA2, via labile chemical bonds, preferably selected from the group of labile chemical bonds comprising: amide, —S—S—, or a bond that can be lysed by a specific enzyme.

According to another useful embodiment of the invention, the active ingredient PA1 or PA2 (e.g. included in a functionalizing graft or complexed by C1) is selected from the group of therapeutic molecules, magnetic compounds, radioactive compounds or those that can become so after activation.

Biological Targeting Compounds

The biological targeting compounds are selected from the following families of biovectors, used in imaging and/or in therapy, preferably from the group of species capable of recognizing and of pairing specifically with biological zones of interest and thus permitting targeting of said zones. They can be, for example: proteins, glycoproteins, lipoproteins, polypeptides, peptides (e.g. RGD), peptidomimetics, dyes, sugars, oligosaccharides, neuromediators, quaternary amines, aptamers, antibodies and combinations of said compounds.

Luminescent Compounds

The luminescent compounds are selected from the group of organic or inorganic fluorophores It goes without saying that each product:

chelating agent C1, C2;
hydrophilic compound;
active ingredient PA1 or PA2;
biological targeting compound;
or luminescent compound;

can possess the characteristic feature of some or all of the other products.

Method

The invention also relates to a method for the production of nanoparticles in particular of the type defined above. This method is characterized in that it comprises steps (a), (b), (c), (d), (e) ((f): optional) defined above; steps (c), (d), (e), (f) can be carried out in a different order or at the same time.

In practice, step (a) consists more precisely of forming a nanoparticle of the core/shell type with a core of lanthanide oxide (by a modified polyol route) and a shell of polysiloxane (by sol/gel), this object has for example a size of around 10 nm (preferably 5 nanometres). A core of lanthanide oxide of very small size (adjustable below 10 nm) can thus be produced in an alcohol by one of the methods described in the following publications (P. Perriat et al., *J. Coll. Int. Sci*, 2004, 273, 191; O. Tillement et al., *J. Am. Chem. Soc.*, 2007, 129, 5076 and P. Perriat et al., *J. Phys. Chem. C*, 2009, 113, 4038).

According to step (b), these cores can be coated with a layer of polysiloxane for example following a protocol described in the following publications (C. Louis et al., *Chem. Mat.*, 2005, 17, 1673 and O. Tillement et al., *J. Am. Chem. Soc.*, 2007, 129, 5076).

In step (c), chelating agents specific to the metal cations in question are grafted on the surface of the polysiloxane; a proportion of them can also be inserted inside the layer but control of the formation of the polysiloxane is complex and simple external grafting gives, at these very small sizes, a sufficient proportion of grafting.

The purification step (d) consists more precisely of separating the nanoparticles from the synthesis residues by a method of dialysis or of tangential filtration, on a membrane having pores of suitable size.

In the next step (e), the core is destroyed by dissolution (for example by altering the pH or by adding complexing molecules to the solution). This destruction of the core then permits dispersal of the polysiloxane layer (by a mechanism of collapse or of slow corrosion), so that finally a polysiloxane object of complex morphology is obtained the characteristic dimensions of which are of the order of magnitude of the thickness of the polysiloxane layer, i.e. much smaller than the objects produced until now. A high content of chelating agents C1 is also obtained, since the latter are grafted initially on the surface of the polysiloxane and at these very small sizes the surface accounts for a very high proportion of the material of the particle, since the ratio of surface area to volume varies as a function of the size as 1/r (radius). In the course of the process of collapse of this structure, other complexes can also attach up to saturation on the newly formed "fresh" surfaces. Thus, contents of complexing agents are reached that are far greater than those that would have been obtained by a conventional surface functionalization of finer silica particles, provided such particles are available.

Withdrawing the core thus makes it possible to pass from a particle size of about 5 nanometres in diameter to a size of about 3 nanometres. Moreover, this operation makes it possible to increase the number of M (e.g. gadolinium) per $nm^3$ in comparison with a theoretical polysiloxane nanoparticle of the same size but comprising M (e.g. gadolinium) solely on the surface.

The number of M for a size of nanoparticle can be evaluated from the atomic ratio M/Si measured by EDX.

Products Derived From the Nanoparticles

The invention also relates to:

A suspension of nanoparticles as defined above and/or obtained by the method described above.

A suspension of nanoparticles as defined above and/or obtained by the method described above, characterized in that it comprises chelating agent $C^1$ free from ions $M^{n+}$ or $D^{m+}$.

A solid material obtained by removal of the liquid, preferably by lyophilization of the suspension of nanoparticles as defined above and/or obtained by the method described above.

An injectable liquid comprising nanoparticles as defined above and/or obtained by the method described above, and/or a suspension of these nanoparticles and/or prepared from the aforementioned solid material.

Applications

The invention also relates to the applications of these nanoparticles, in particular including:

A composition as a diagnostic aid, preferably a contrast composition, characterized in that it comprises nanoparticles as defined above and/or obtained by the method described above and/or the aforementioned suspension and/or prepared from the solid material defined above.

A therapeutic composition, characterized in that it comprises nanoparticles as defined above and/or obtained by the method described above and/or the aforementioned suspension and/or prepared from the solid material defined above.

A therapeutic composition comprising nanoparticles as defined above and/or obtained by the method described above and/or the aforementioned suspension and/or prepared from the solid material defined above, for the treatment of cancers or neurodegenerative diseases, in particular for targeting sites to be treated.

A cellular labelling composition, characterized in that it comprises nanoparticles as defined above and/or obtained by the method described above and/or the aforementioned suspension and/or prepared from the solid material defined above.

Materials and Methods

The size of the nanoparticles in colloidal suspension is measured by photon correlation spectroscopy (PCS) on a Zetasizer Nano-S from Malvern.

The particle size can also be measured by transmission electron microscopy (TEM), on a JEOL 2010 microscope with an acceleration voltage of 200 kV. One drop of diluted colloidal solution is placed on a carbon grid for the analysis.

The solutions are centrifuged using an Allegra 25R centrifuge from Beckman Coulter, at a speed of 4100 rpm.

In the context of purification, tangential filtration of the solutions is performed through a 5 kDa membrane, in 20 mL Vivaspin tubes from Sartorius Stedim Biotech, until a dilution of the impurities greater than 1000 is obtained. For this, the Vivaspin tubes are also centrifuged at 4100 rpm.

The particles are lyophilized under dynamic vacuum at 0.15 mbar and −2° C. in a CHRIST Alpha 1-2 lyophilizer.

The chemical analyses by X-ray diffraction (EDX) are performed on a Philips XL20 scanning electron microscope. For each sample, one drop of aqueous solution is deposited on a carbon support. After drying, the surface is metallized with a 10 nm thick layer of gold. For chemical analysis, three measurements are averaged, on three zones of about 50 μm×50 μm. The percentages of each element are obtained as atomic percentages.

The signal from the particles in relaxometry is measured using a Bruker Minispec MQ60 NMR analyser, with a magnetic field of 1.4 T.

EXAMPLE 1

Synthesis of the Gadolinium Oxide Core

A solution is prepared by dissolving a quantity of 11 g/L of gadolinium chloride salt ($GdCl_3$, $6H_2O$) in a volume of 375 mL of diethylene glycol (DEG). 375 mL of a soda solution at 0.1 mol/L in DEG is added to the solution obtained, at room temperature, in 15 h.

Figure 3:
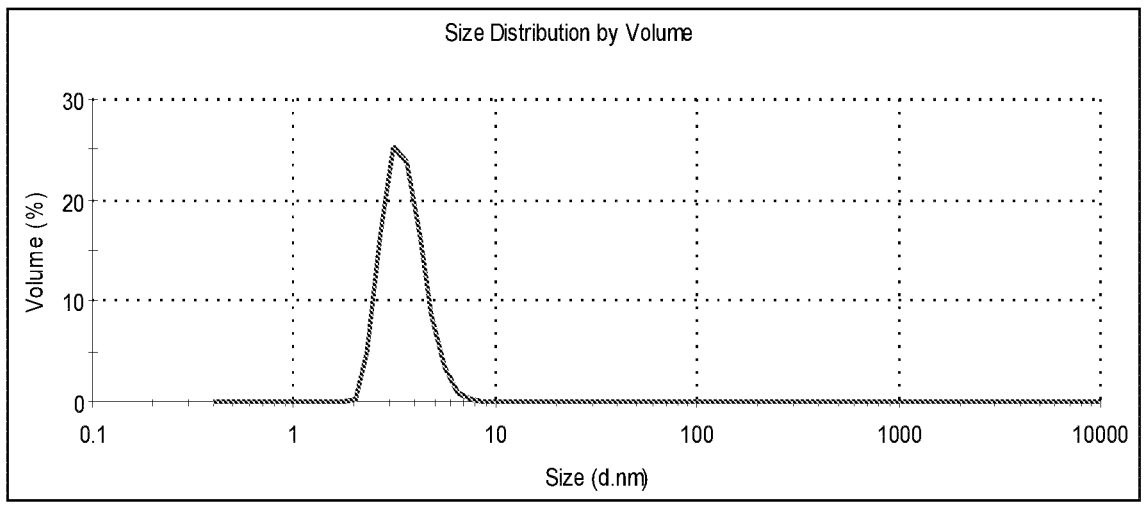

The attached FIG. 3 shows the size distribution of the gadolinium oxide cores, measured in DEG by PCS; mean value: 3.6 nm.

EXAMPLE 2

Functionalization of the Gadolinium Oxide Cores with DTPABA

Figure 4:
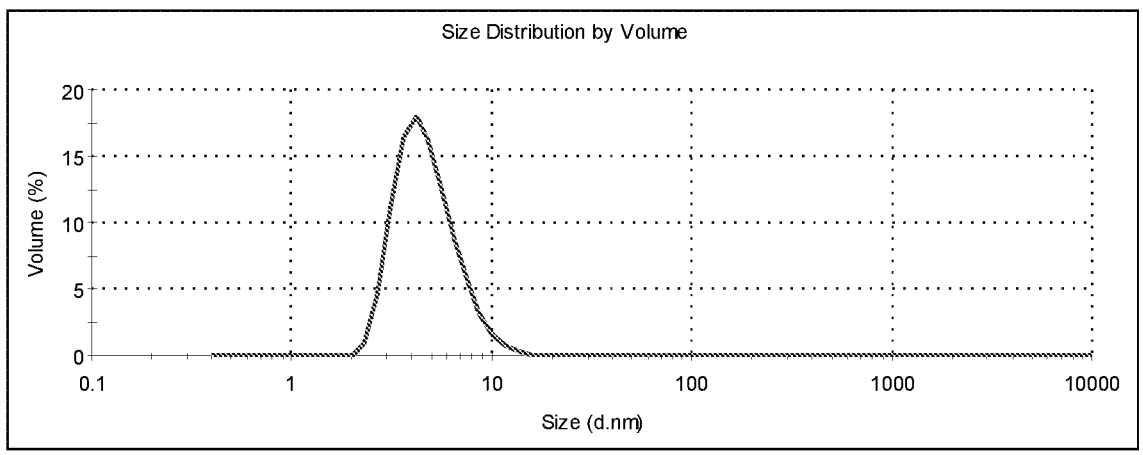

A layer of functionalized polysiloxane is synthesized by the sol-gel process around the gadolinium oxide cores from Example 1. For this purpose, the 750 mL solution of cores is heated to 40° C. in an oil bath, with stirring. 787 μL of APTES, 502 μL of TEOS and 1913 μL of an aqueous solution of triethylamine at 0.1 mol/L are added to the solution of cores. These additions are repeated a second time after waiting 24 h. The solution is then stirred at 40° C. for 48 h. Core-shell particles are obtained with a size of about 5 nm, with amine functions on the surface. FIG. 4 shows the size distribution of the polysiloxane-coated cores, measured in DEG by PCS; mean value: 4.9 nm.

Then 3.135 g of DTPABA is dispersed in 150 mL of dimethyl sulphoxide (DMSO). Then the 750 mL of solution of gadolinium oxide cores is added to the solution of DTPABA. The mixture is stirred for 24 h.

The nanoparticles are then precipitated by centrifugation in four 500-mL vessels of acetone. Then the acetone is removed, and the particles are redispersed in 100 mL of water in total. They are then purified by tangential filtration. The large size impurities are removed by filtration by means of a syringe, through a 0.2 μm membrane.

Figure 5:
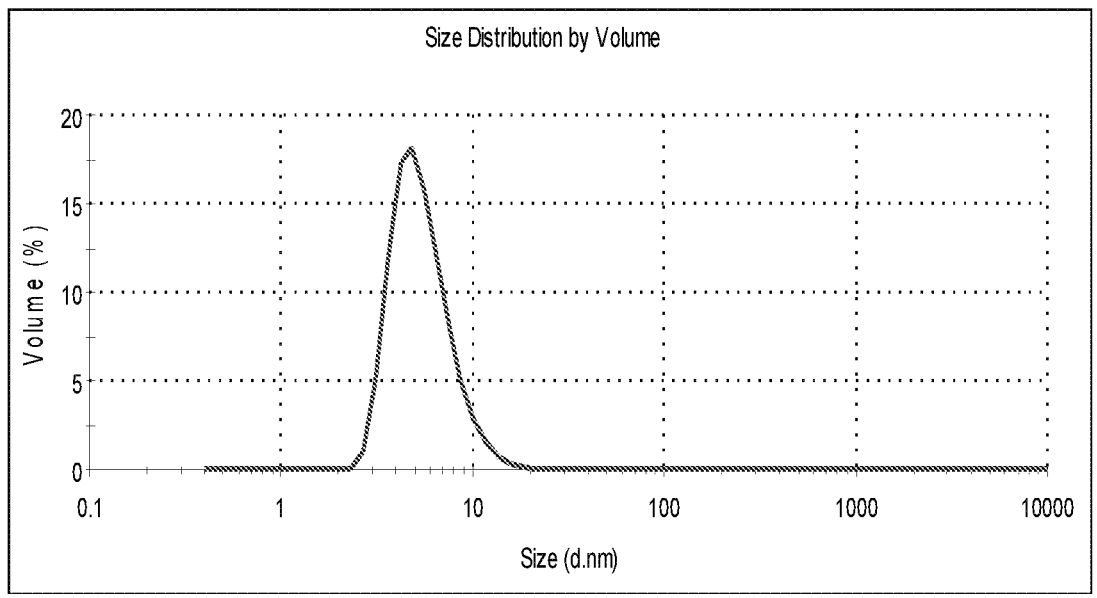

Particles are obtained with a size of about 5.5 nm. FIG. 5 shows the size distribution of the DTPABA-functionalized polysiloxane-coated cores, measured in water by PCS; mean value: 5.6 nm.

Figure 6:
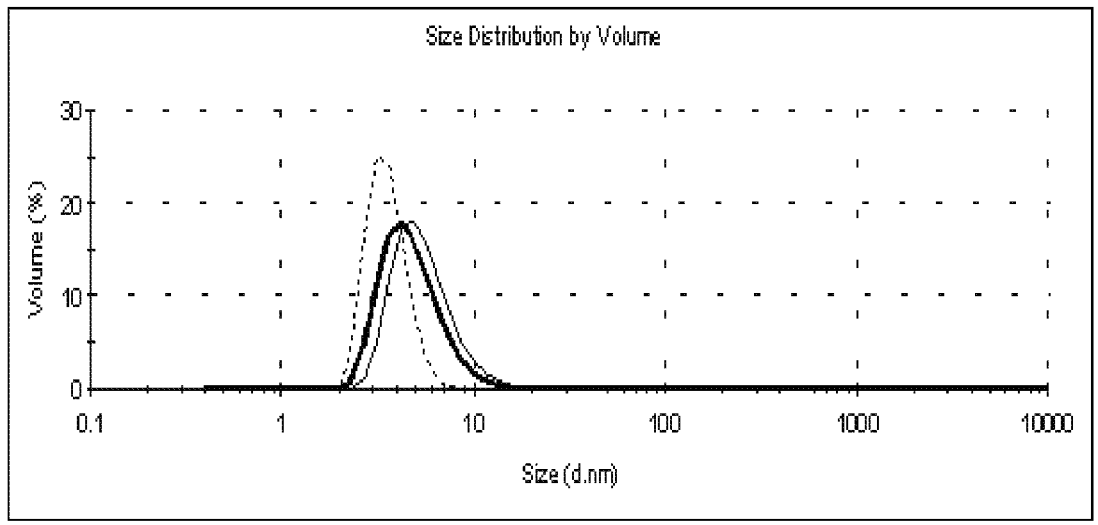

The attached FIG. 6 shows monitoring of the synthesis by granulometry: dashed line (----) size distribution of the cores alone; thick solid line (—) size distribution of the polysiloxane-coated cores; thin solid line (—) size distribution of the polysiloxane-coated, DTPABA-functionalized cores.

Figure 7:
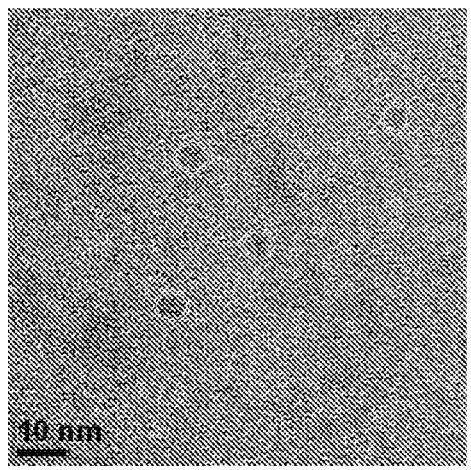

The attached FIG. 7 shows the TEM image of the DTPABA-functionalized particles; the sizes observed are between 4 and 6 nm.

The aqueous solution of nanoparticles can be stored for several months in a refrigerator after lyophilization, in hermetically sealed tablet bottles.

Chemical analysis, performed by inductively-coupled plasma-mass spectroscopy (ICP-MS) at the Solaize Central Analysis Service, gives the following results as atomic percentages: carbon 70.6%, nitrogen 14.3%, gadolinium 4.9%.

EXAMPLE 3

Dissolution of the Core of DTPABA-Functionalized Gadolinium Oxide Particles by Means of Hydrochloric Acid Concentrated hydrochloric acid is added to the particles from Example 2, dispersed in water, until a pH equal to 2.5 is obtained. It is stirred overnight.

The solution is purified by tangential filtration, to remove the $Gd^{3+}0$ ions that were dissolved from the core of the particles. Particles are obtained with a size of about 3.5 nm.

Figure 8:
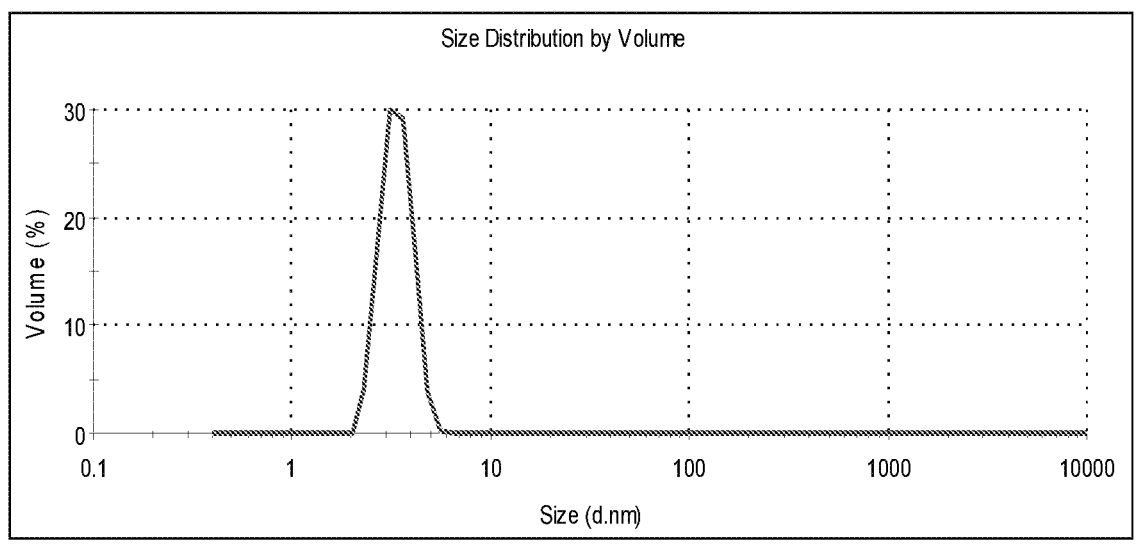

The attached FIG. 8 shows the size distribution of the particles reduced in size with hydrochloric acid, measured in water by PCS; mean value: 3.4 nm.

The signal from the particles in relaxometry $r_1=1/T_1$ decreased by 27%. Considerable chemical attack was observed with forced dissolution by acid attack. This is confirmed by the large decrease in relaxometry.

Moreover, chemical analysis by EDX gives a gadolinium/silicon atomic ratio of 22.1%. Relative to the particles from Example 2, it is observed that 54% of the gadolinium was dissolved by acid attack.

EXAMPLE 4

Dissolution of the Core of DTPABA-Functionalized Gadolinium Oxide Particles by Means of Free DTPA Free DTPA is added in large excess to the particles from Example 2, dispersed in water. The solution pH is adjusted to 7. It is stirred overnight.

Figure 9:
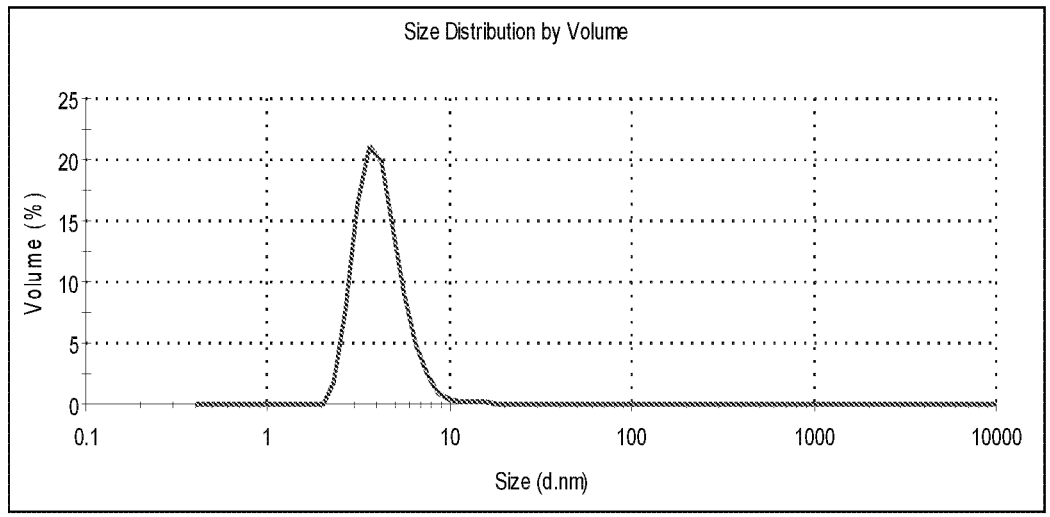

The solution is purified by tangential filtration, to remove the $Gd^{3+}$ ions that were dissolved from the core of the particles, and complexed by the free DTPA. Particles are obtained with a size of about 4 nm. The attached FIG. 9 shows the size distribution of the particles reduced in size with the addition of DTPA, measured in water by PCS; mean value: 4.3 nm.

Moreover, the signal from the particles in relaxometry $r_1$ decreased by 71% relative to the particles from Example 2. Very marked chemical attack of the core by forced dissolution by complexing is observed. A loss of $Gd^{3+}$ complexed on the surface-grafted DTPA is also probable, which explains the larger decrease in the relaxometry signal relative to Example 3.

Moreover, chemical analysis by EDX gives a gadolinium/silicon atomic ratio of 10.8%. Relative to the particles from Example 2, it is observed that 78% of the gadolinium has therefore been removed by complexing the DTPA.

In order to evaluate the loss of $Gd^{3+}$ complexed on the surface-grafted DTPA, it was decided to add fresh $Gd^{3+}$ ions to fill these complexes again. A quantity of $Gd^{3+}$ ions equivalent to what was lost in the preceding step is dissolved in water. The pH of this solution is adjusted to 6.5. Then this solution is added to the nanoparticles of reduced size. It is stirred overnight.

Figure 10:
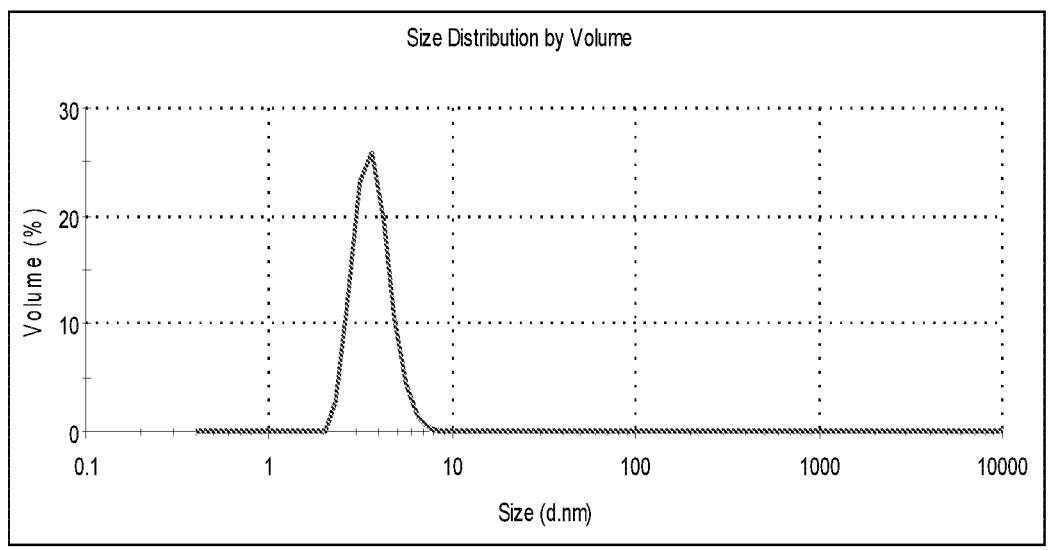

The solution is purified by tangential filtration, to remove the $Gd^{3+}$ ions that have not been complexed by the DTPA. Particles are obtained with a size of about 3.5 nm. The attached FIG. 10 shows the size distribution of the particles reduced in size by adding DTPA, and then adding Gd3+, measured in water by PCS; mean value: 3.7 nm.

Moreover, the signal from the particles in relaxometry r1 increased by 123% relative to the particles of reduced size. We therefore observe filling of the DTPAs that remained empty with the $Gd^{3+}$ ions supplied to the solution. The particle size remains almost unchanged.

Figure 11:
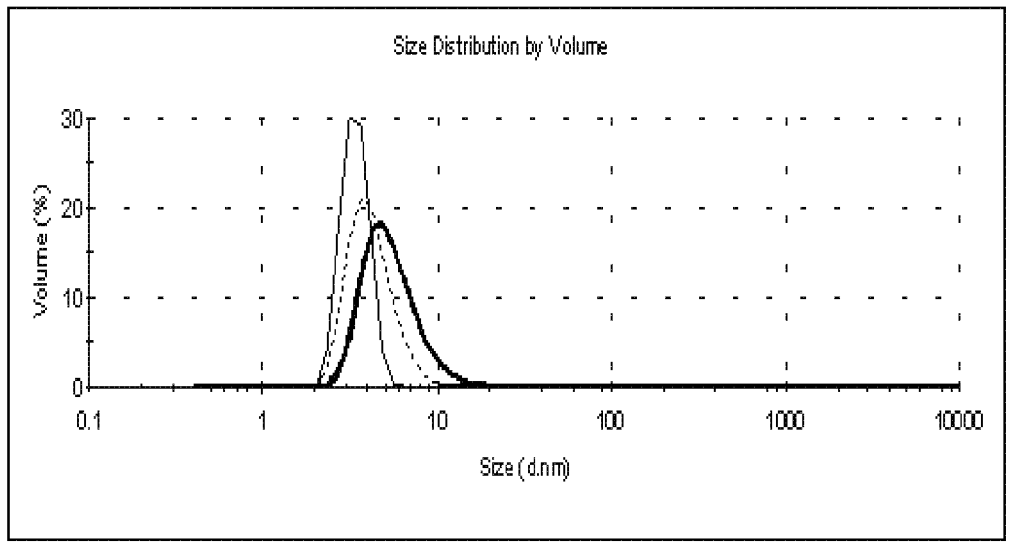

FIG. 11 summarizes the above size reduction experiments: thick solid line ( ▬ ) size distribution of the initial particles; thin solid line ( — ) size distribution of the particles reduced in size with HCl; dashed line ( ---- ) size distribution of the particles reduced in size with free DTPA.

EXAMPLE 5

Dissolution of the Polysiloxane-Coated Gadolinium Oxide Cores, Directly by Adding DTPABA in Large Excess Particles are synthesized according to the protocol described in Example 2, but varying the quantity of DTPABA added for functionalization. This quantity varies from a DTPABA/APTES ratio of 0.5 to 3. The number of APTES is selected as a parameter as it represents the number of potentially reactive functions on the surface of the particles.

Figure 23:
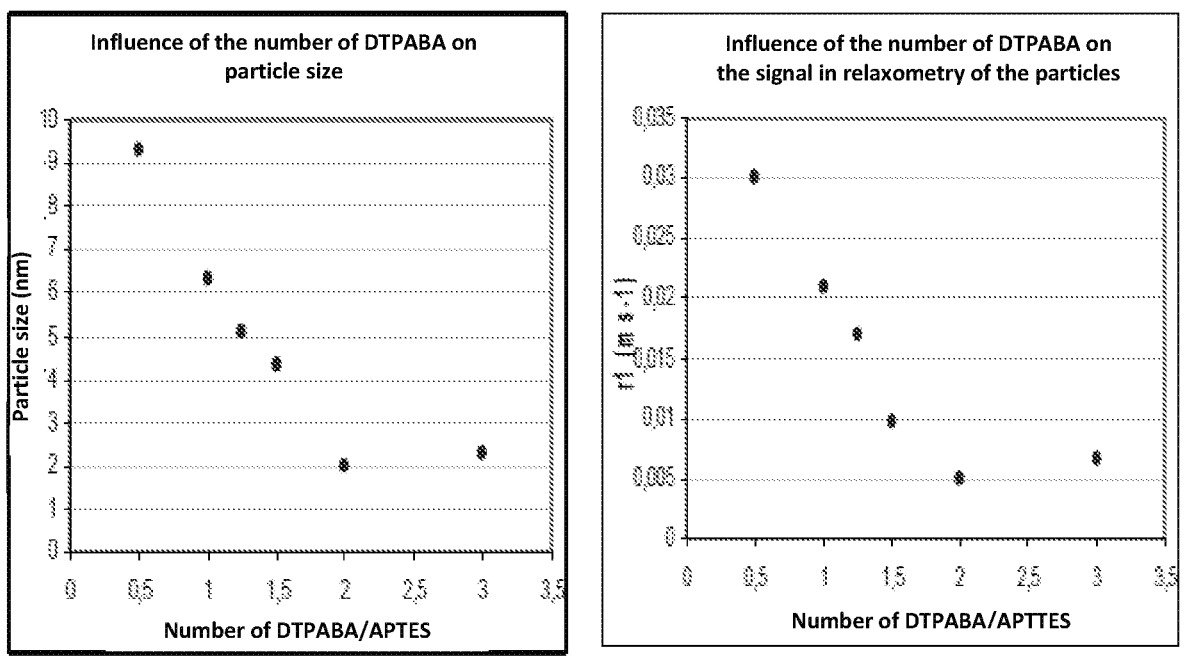

The attached FIG. 23 shows the variation of the size (on the left) and of the relaxometry signal (on the right), with the number of DTPABA added for functionalization. The relaxometry signal is measured in aqueous solution diluted 10-fold. For small quantities of DTPABA, the nanoparticles remain large. For large quantities of DTPABA, in contrast, the particle size seen in PCS decreases, as the core of the particles dissolves. For DTPABA/APTES values of 2 and 3, the core of the particles is completely destroyed, and the particle size remains at about 2 nm. The relaxometry signal of the particles decreases in proportion to the size, which is reflected in the proportional decrease in the quantity of gadolinium present in the cores.

EXAMPLE 6

Functionalization of the Gadolinium Oxide Cores with DOTA-NHS and Purification

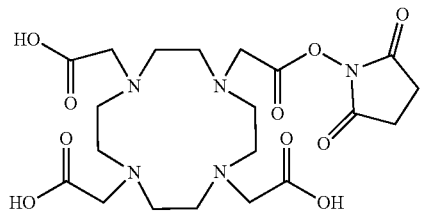 [SMILES: O=C(O)CN1CCN(CC(=O)O)CCN(CC(=O)ON2C(=O)CCC2=O)CCN(CC(=O)O)CC1]

Figure 12:
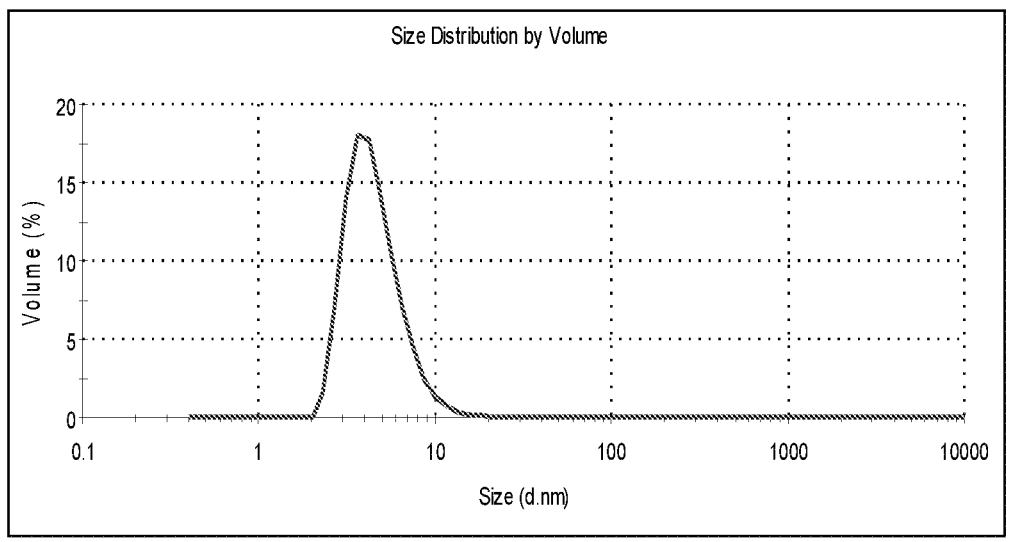

A layer of functionalized polysiloxane is synthesized by the sol-gel process around the gadolinium oxide cores from Example 1. For this purpose, the 750 mL solution of cores is heated to 40° C. in an oil bath, with stirring. 787 µL of APTES coupled to 0.75 mg of fluorescein isothiocyanate (FITC), 502 µL of TEOS and 1913 µL of an aqueous solution of triethylamine at 0.1 mol/L are added to the solution of cores. These additions are repeated a second time after waiting 24 h, and a third time after waiting 48 h. The solution is then stirred at 40° C. for 48 h. Core-shell particles are obtained with a size of about 5 nm, with amine functions on the surface. The attached FIG. 12 shows the size distribution of the polysiloxane-coated cores, measured in DEG by PCS; mean value: 4.7 nm.

1.12 g of DOTA-NHS is dispersed in 20 mL of anhydrous ethanol. Then 100 mL of the solution of gadolinium oxide cores is added to the solution of DOTA-NHS. The mixture is stirred for 24 h.

Figure 13:
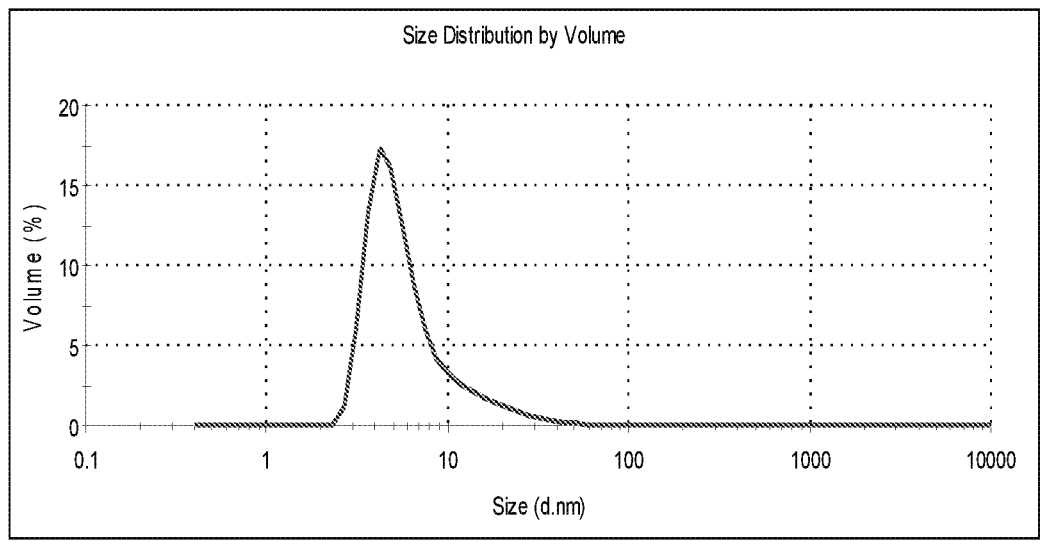

The nanoparticles are then precipitated in 500 mL of acetone. Then the acetone is removed, and the particles are redispersed in 20 mL of water. They are then purified by tangential filtration. The large size impurities are removed by filtration by means of a syringe, through a 0.2 µm membrane. Particles are obtained with a size of about 7 nm. The attached FIG. 13 shows the size distribution of the DOTA-NHS-functionalized polysiloxane-coated cores, measured in water by PCS; mean value: 6.8 nm.

Figure 14:
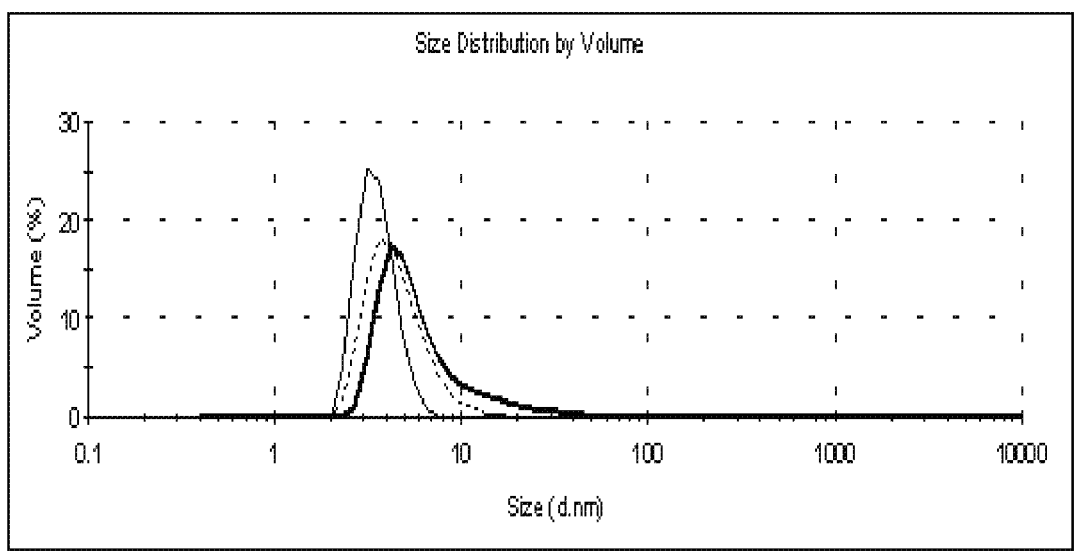

The attached FIG. 14 shows monitoring of the preceding synthesis by granulometry: thin solid line ( — ) size distribution of the cores alone; dashed line ( ---- ) size distribution of the polysiloxane-coated cores; thick solid line ( ▬ ) size distribution of the polysiloxane-coated and DOTA-NHS-functionalized cores.

EXAMPLE 7

Dissolution of the Core of the DOTA-NHS-Functionalized Gadolinium Oxide Particles by Means of Free DTPA Free DTPA is added in large excess to the particles from Example 6, dispersed in water. The pH of the solution is adjusted to 7. It is stirred overnight.

Figure 15:
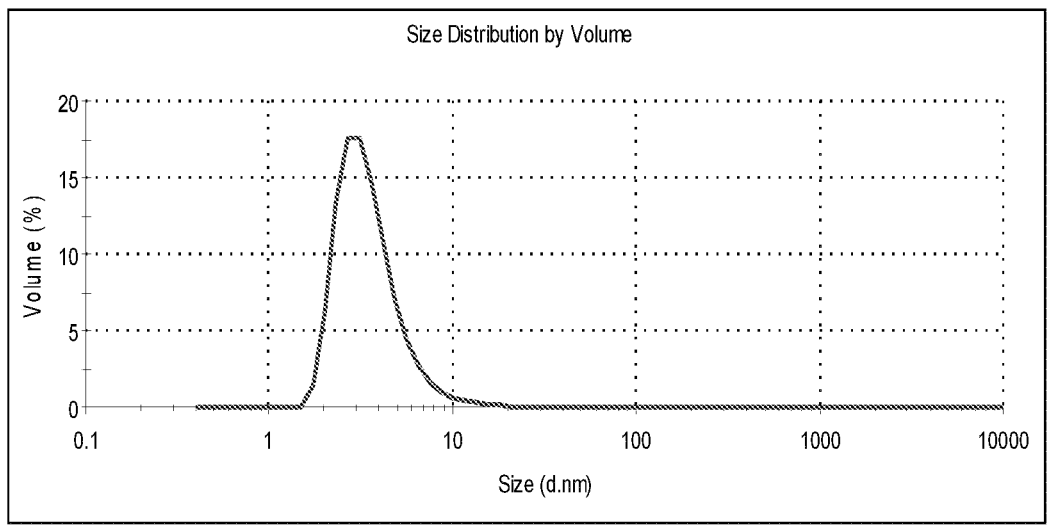

The solution is purified by tangential filtration, to remove the Gd³+ ions that were dissolved from the core of the particles. Particles are obtained with a size of about 3.5 nm. The attached FIG. 15 shows the size distribution of the particles reduced in size by adding DTPA, measured in water by PCS; mean value: 3.7 nm.

Moreover, the signal from the particles in relaxometry r1 has decreased by 84%, which is reflected in a large decrease in the quantity of gadolinium present in the particles.

Figure 16:
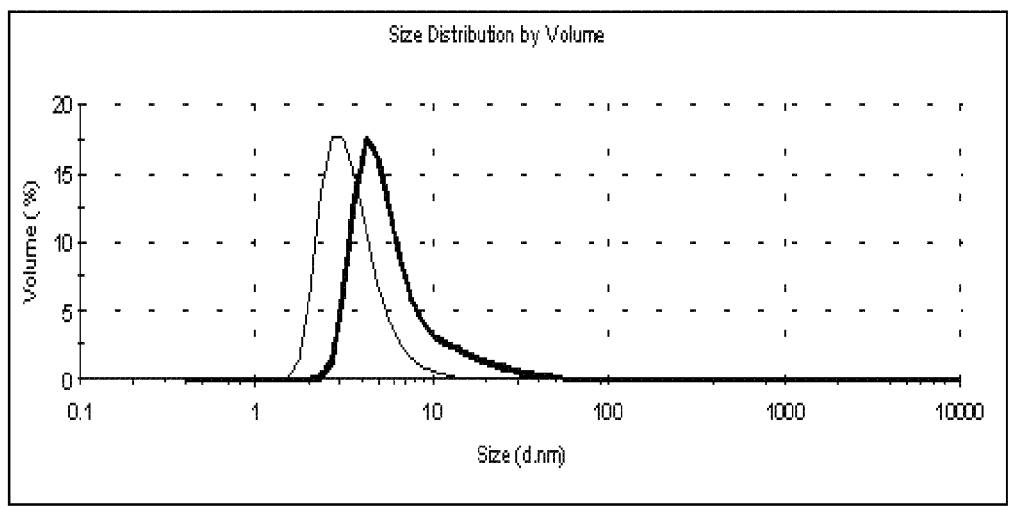

The attached FIG. 16 shows the size reduction experiment: thick solid line ( ▬ ) size distribution of the initial particles; thin solid line ( ▬ ) size distribution of the particles reduced in size with free DTPA.

EXAMPLE 8

Functionalization of the Gadolinium Oxide Cores with DOTAGA Anhydride

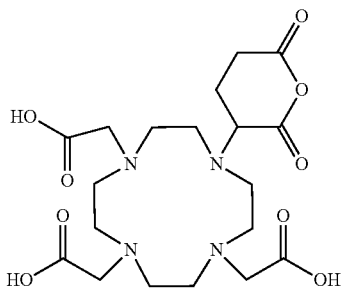 [SMILES: O=C(O)CN1CCN(CC(=O)O)CCN(C2CCC(=O)OC2=O)CCN(CC(=O)O)CC1]

Figure 17:
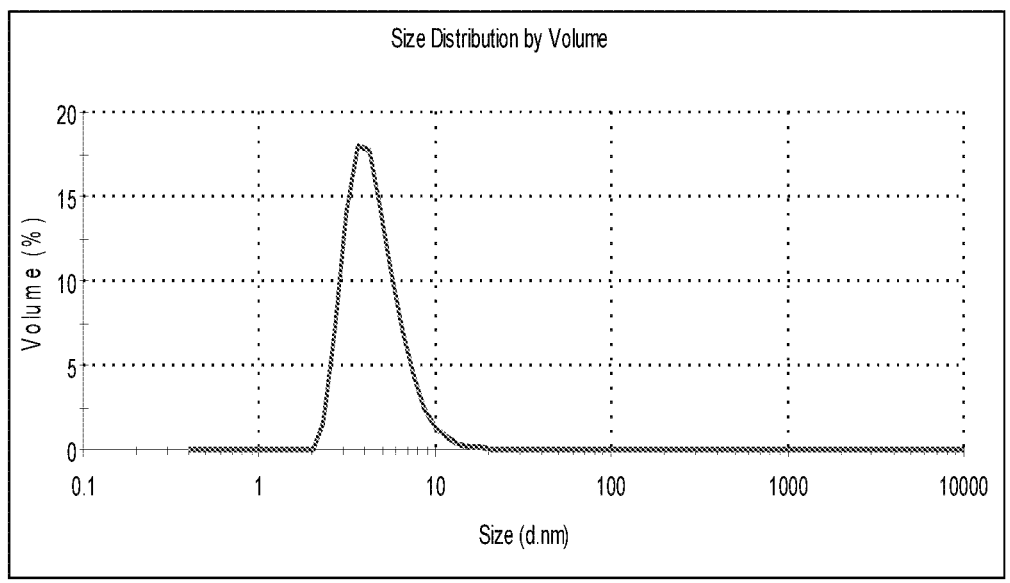

A layer of functionalized polysiloxane is synthesized by the sol-gel process around the gadolinium oxide cores from Example 1. For this purpose, the 750 mL solution of cores is heated to 40° C. in an oil bath, with stirring. 787 μL of APTES coupled to 0.75 mg of FITC, 502 μL of TEOS and 1913 μL of an aqueous solution of triethylamine at 0.1 mol/L are added to the solution of cores. These additions are repeated a second time after waiting 24 h, and a third time after waiting 48 h. The solution is then stirred at 40° C. for 48 h. Core-shell particles are obtained with a size of about 4.5 nm, with amine functions on the surface. The attached FIG. 17 shows the size distribution of the polysiloxane-coated cores, measured in DEG by PCS; mean value: 4.7 nm.

Figure 18:
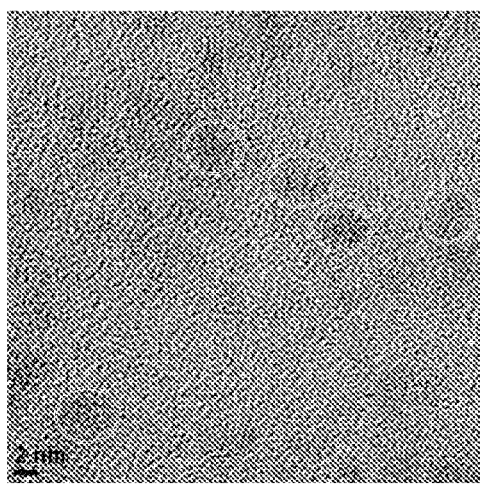

The particle size is also measured by TEM. The attached FIG. 18 shows the TEM image of the polysiloxane-coated cores, dispersed by means of polyethylene glycol grafting; the sizes observed are between 4 and 5 nm.

Next, 0.619 g of DOTAGA anhydride is dispersed in 20 mL of DMSO. Then 100 mL of the solution of gadolinium oxide cores is added to the solution of DOTAGA anhydride. The mixture is stirred for 24 h.

EXAMPLE 9

Figure 19:
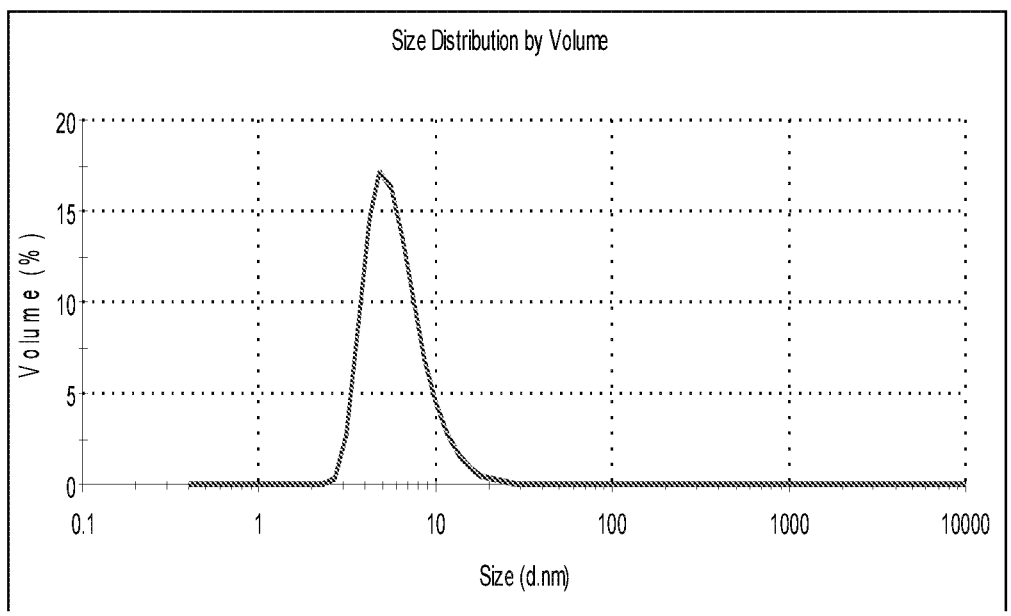

Purification of the Gadolinium Oxide Particles Functionalized with DOTAGA Anhydride The nanoparticles from Example 8 are precipitated in 500 mL of acetone. Then the acetone is removed, and the particles are redispersed in 20 mL of water. They are then purified by tangential filtration. Large size impurities are removed by filtration by means of a syringe, through a 0.2 μm membrane. Particles are obtained with a size of about 6.5 nm. The attached FIG. 19 shows the size distribution of the polysiloxane-coated cores, functionalized with DOTAGA anhydride, measured in water by PCS; mean value: 6.3 nm.

The attached FIG. 1 shows the TEM image of the polysiloxane-coated cores, functionalized with DOTAGA anhydride; the sizes observed are between 3 and 5 nm. The molecules of DOTAGA are not visible in TEM, only the coated cores are seen.

Figure 20:
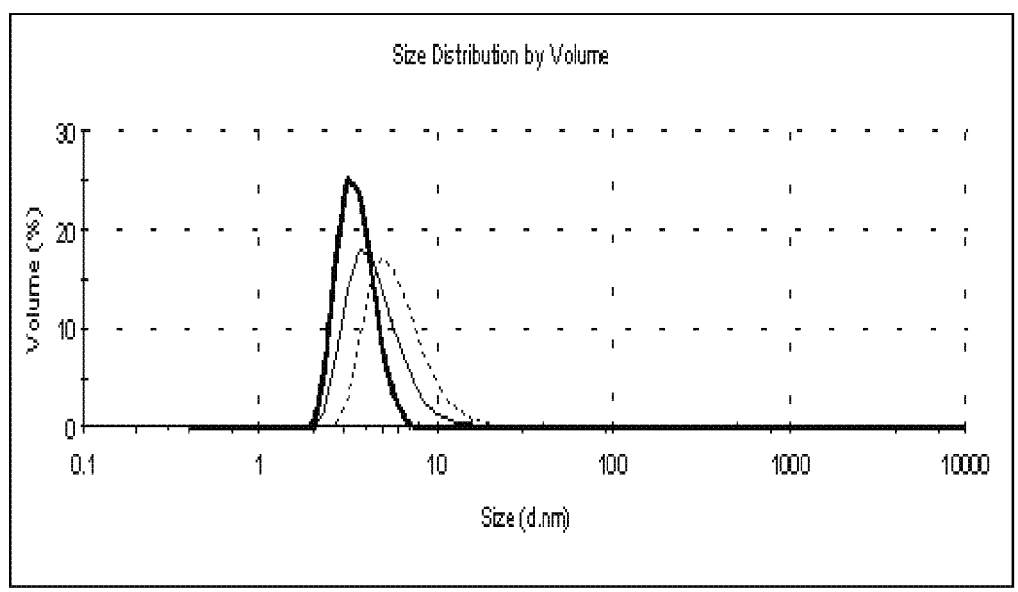

The attached FIG. 20 shows monitoring of the synthesis by granulometry: thick solid line ( ▬ ) size distribution of the cores alone; thin solid line ( ▬ ) size distribution of the polysiloxane-coated cores; dashed line ( ---- ) size distribution of the polysiloxane-coated cores functionalized with DOTAGA anhydride.

Chemical analysis by EDX gives a gadolinium/silicon atomic ratio of 57.2%.

The solution of nanoparticles can be stored for several months in a refrigerator after lyophilization.

EXAMPLE 10

Dissolution of the Core of the Gadolinium Oxide Particles Functionalized with DOTAGA Anhydride by Means of Free DTPA A solution of DTPA in water is prepared, then the pH of the solution is adjusted to 6. A solution of DTPA is added in large excess to the particles from Example 8, dispersed in the mixture of solvents DEG and DMSO. It is stirred overnight.

Figure 21:
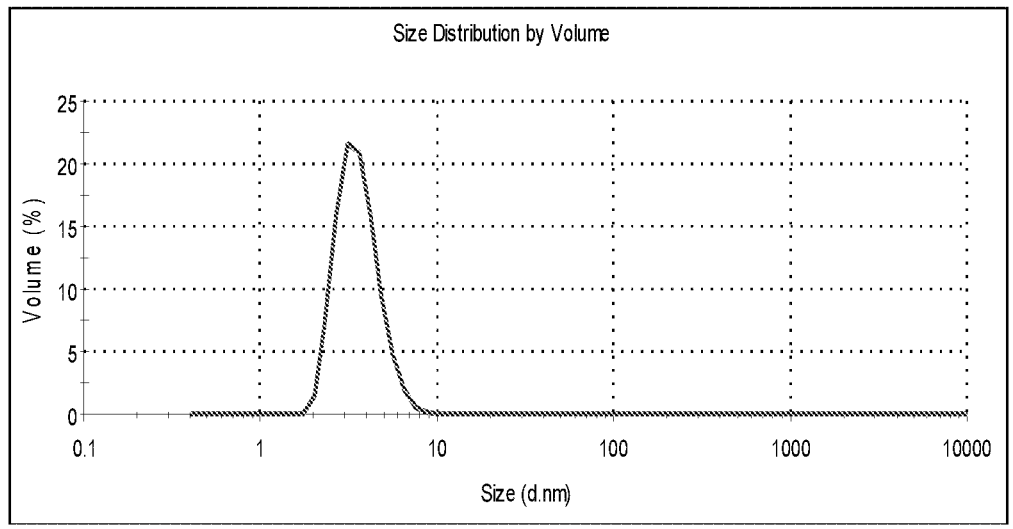

The solution is purified by tangential filtration, to remove the Gd³+ ions that were dissolved from the core of the particles. On the same occasion, the particles are passed through water. Particles are obtained with a size of about 3.5 nm. The attached FIG. 21 shows the size distribution of the particles reduced in size by adding DTPA, measured in water by PCS; mean value: 3.6 nm.

The attached FIG. 2 shows the TEM image of the particles the size of which was reduced. The image was obtained under the same conditions as the previous images. Moreover, local chemical analysis indicates the presence of gadolinium in a significant quantity at the place observed, but no particle can be seen there. The particles therefore no longer have a crystallized core at this stage.

Figure 22:
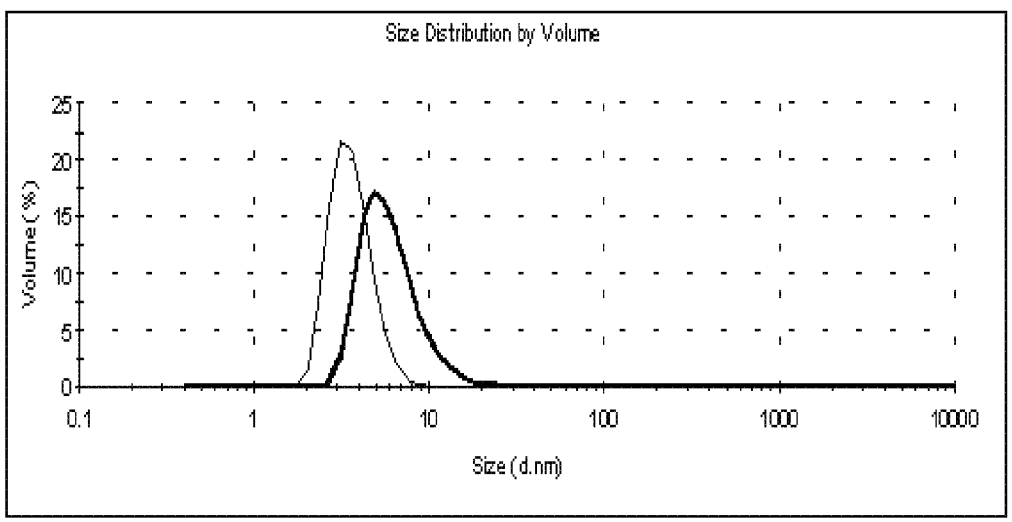

The attached FIG. 22 shows the size reduction experiment: thick solid line ( ▬ ) size distribution of the initial particles; thin solid line ( ▬ ) size distribution of the particles reduced in size with free DTPA.

Furthermore, the signal from the particles in relaxometry r1 has decreased by 71%. This is reflected in a large decrease in the quantity of gadolinium present in the particles.

Moreover, chemical analysis by EDX gives a gadolinium/silicon atomic ratio of 24.1%. Relative to the particles from Example 9, it is observed that 58% of the gadolinium has therefore been dissolved by complexing the DTPA.

EXAMPLE 11

Direct Synthesis of Coreless Nanoparticles Functionalized with DOTAGA Anhydride

Nanoparticles are synthesized according to the protocol described in Example 8, but the surface functionalization is performed with a large excess of DOTAGA anhydride (2 DOTAGA/Gd). Thus, all the Gd atoms are directly complexed by molecules of DOTAGA, and a significant proportion of non-complexed DOTAGA remains.

The solution is placed in a 4-6 kDa dialysis membrane, and is purified by dialysis in a ten-fold larger volume of deionized water. The dialysis bath is renewed twice, after 24 h and 48 h. The dialyse is stopped after 72 h.

Figure 24:
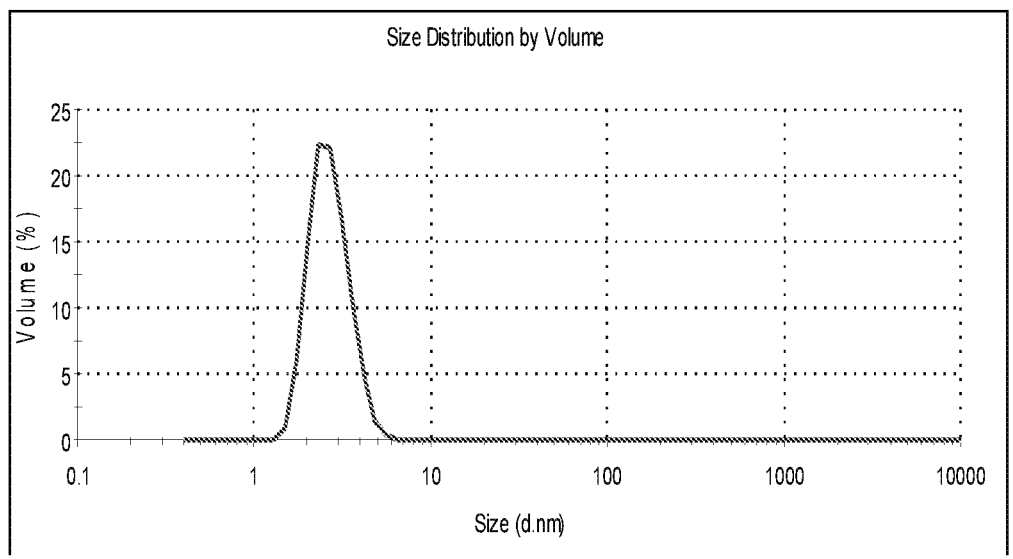

The contents of the dialysis membranes are recovered. The solution appears slightly cloudy, it is therefore filtered through a 0.2 μm filter to remove large size impurities and particles. The final size of the nanoparticles is about 3 nm. The attached FIG. 24 shows the size distribution of the particles functionalized with DOTAGA anhydride, measured in water by PCS; mean value: 2.7 nm.

Moreover, when the particles are centrifuged in Vivaspin tubes, it is observed that they are not retained by a 10 kDa membrane. They are, however, retained by a 5 kDa membrane.

Chemical analysis by EDX gives a gadolinium/silicon atomic ratio of 29.3%.

Finally, the TEM images show that no core is visible in these particles, whereas local chemical analysis proves the presence of gadolinium in these zones.

The solution of nanoparticles can be stored for several months in a refrigerator after lyophilization.

EXAMPLE 12

Doping of the Magnetic Signal of the Coreless Particles Functionalized with DOTAGA Anhydride Gadolinium chloride is dissolved in water, and the pH of the solution is adjusted to 6. The $Gd^{3+}$ ions thus obtained are added to the particles from Example 11, in excess. The solution is stirred for 24 h. The solution is purified by tangential filtration to remove any $Gd^{3+}$ ions that have not become attached to the molecules of DOTAGA.

After the treatment with $Gd^{3+}$ ions, the relaxometry signal r1 of the particles has increased by 66%. Moreover, chemical analysis by EDX on these particles gives a gadolinium/silicon atomic ratio of 47.5%, or an increase by 62% relative to the particles from Example 11. These two measurements, which are in agreement, show that there were indeed free molecules of DOTAGA on the surface of the particles, and that these DOTAGA were able to serve for complexing the free $Gd^{3+}$ ions.

EXAMPLE 13

Angiography

A lyophilized batch of nanoparticles from Example 12, containing 7 μmol of gadolinium, was redispersed in 90 μL of water. A Fisher rat was anaesthetized with isoflurane® (anaesthetic gas), and the solution of nanoparticles was injected in the caudal vein. The rat then underwent an MRI examination (sequence t1) for an angiographic study. A considerable increase in the signal was observed at the level of the middle cerebral artery in this animal compared with the control animals.

EXAMPLE 14

Europium Doping of the Coreless Particles Functionalized with DOTAGA Anhydride

Europium chloride is dissolved in water, and the pH of the solution is adjusted to 6. The $Eu^{3+}$ ions thus obtained are added to the particles from Example 11, in excess. The solution is stirred for 24 h. The solution is purified by tangential filtration in order to remove $Eu^{3+}$ ions that have not become attached to the molecules of DOTAGA.

After the treatment with the $Eu^{3+}$ ions, chemical analysis of these particles by EDX gives a gadolinium/silicon atomic ratio of 20.1%, and a europium/silicon ratio of 28.8%. This measurement shows that there were indeed free molecules of DOTAGA on the surface of the particles, and that they could have been chelated by adding free $Eu^{3+}$ ions. Moreover, the overall rare earths/silicon ratio obtained is 48.9%, which is consistent with the rare earths/silicon ratio of the particles from Example 12, which is 47.5%. This gives an estimate of the total number of DOTAGA on the surface of the particles.

Figure 25:
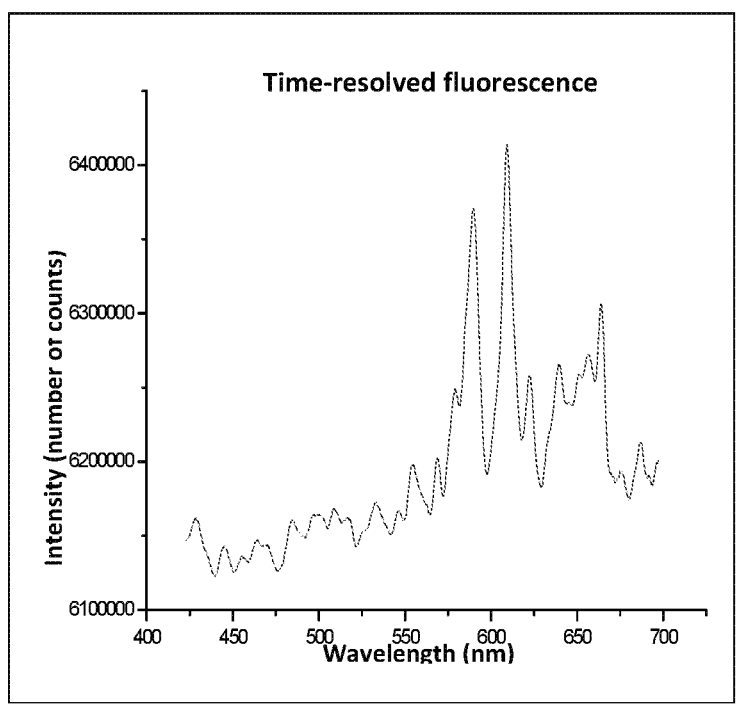

A time-resolved fluorescence measurement shows that the $Eu^{3+}$ ions are mainly in the complexed state in the solution. The attached FIG. 25 shows this fluorescence spectrum. The equipment used for time-resolved fluorescence is an instrument made by the company AXINT, for the specific needs of the laboratory.

Similar doping experiments were performed with copper and gallium ions, and showed that it is also possible to complex these ions in free DOTAGA.

EXAMPLE 15

Direct Synthesis of Coreless Nanoparticles Functionalized with DOTAGA Anhydride, with Surface Saturation of the DOTAGA with Gadolinium Nanoparticles are synthesized according to the protocol described in Example 8, but the surface functionalization is performed with a large excess of DOTAGA anhydride (2 DOTAGA/Gd). Thus, all the Gd atoms are directly consumed by the DOTAGA complexes.

Figure 31:
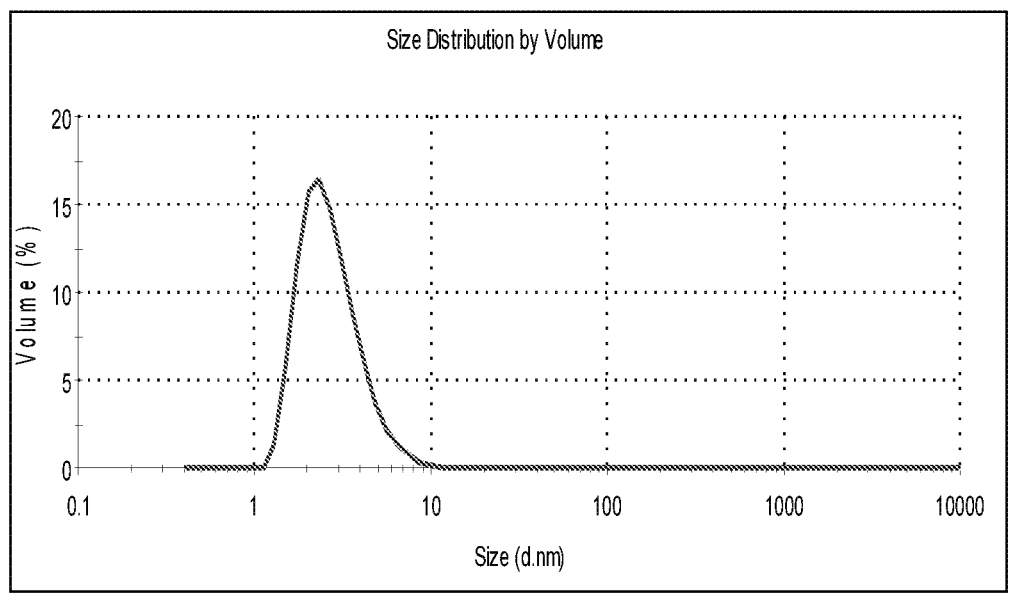

The nanoparticles are precipitated in 500-mL vessels of acetone. Then the acetone is removed, and the particles are redispersed in water. They are then purified by tangential filtration. The large size impurities are removed by filtration by means of a syringe, through a 0.2 μm membrane. The attached FIG. 31 shows the size distribution of the particles functionalized with DOTAGA anhydride, measured in water by PCS; mean value: 2.8 nm.

The solution of nanoparticles can be stored for several months in a refrigerator after lyophilization.

EXAMPLE 16

Cellular Labelling

Human T2 lymphocytes (ATCC No. CRL-1992™) were incubated in HBSS (Hank's Balanced Salt Solution) for 1 h with the nanoparticles from Example 15 (NP15), with gadolinium concentrations of 0.2; 0.5 and 1 mM. After incubation, the cells were washed twice in HBSS.

The viability was evaluated by counting on a Malassez grid after adding Trypan Blue (dilution to ½0th). For the three gadolinium concentrations present in the incubation medium, cell viability was good, being above 90%. In this range of concentrations, the nanoparticles from Example 15 were not toxic.

Figure 29:
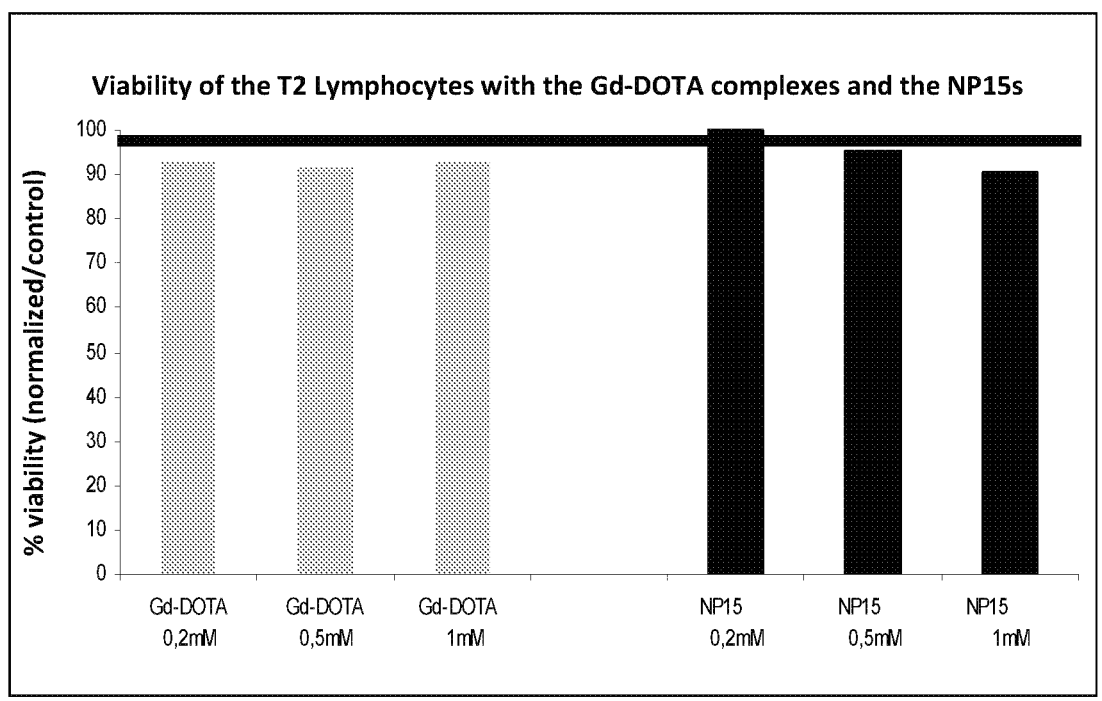

The attached FIG. 29 shows the viability of the T2 lymphocytes for each incubation condition.

Figure 30:
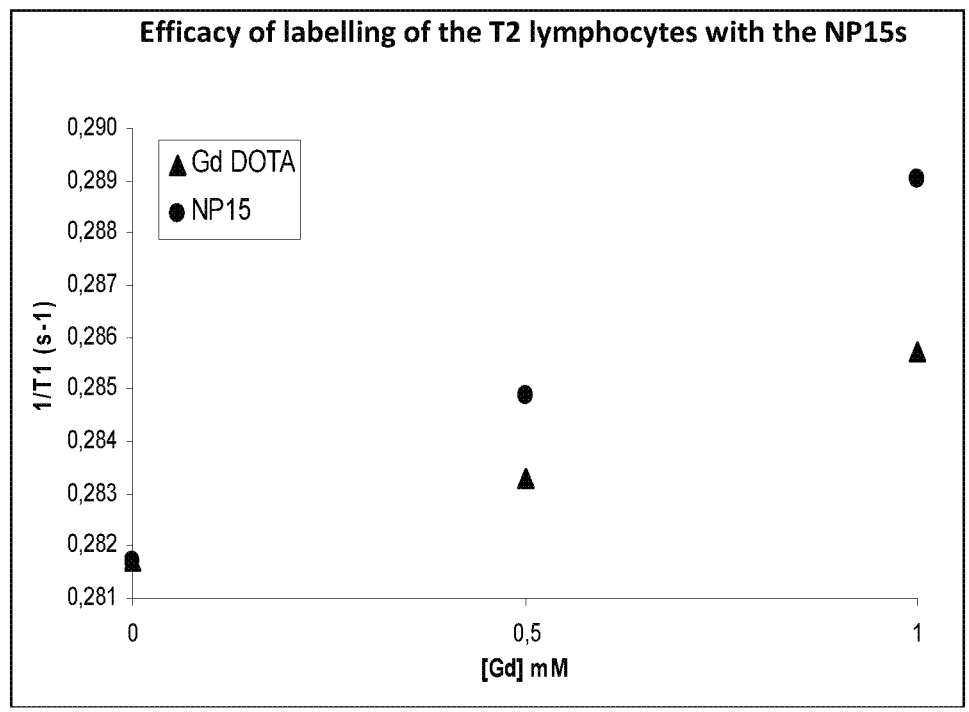

After evaluation of the viability, the cells were fixed in a 4% solution of paraformaldehyde and then the efficacy of labelling was evaluated by measuring the longitudinal relaxation time $T_1$. The higher $r_1=1/T_1$, the better the labelling. The labelling with the nanoparticles from Example 15 was therefore better than with the Gd-DOTA complexes. At a concentration of 1 mM, the increase in signal was 15% with 50 000 cells/mm³. The attached FIG. 30 shows the efficacy of labelling of the particles from Example 15 in comparison with the Gd-DOTA complexes, and as a function of the gadolinium concentration.

Moreover, the relaxivity of the particles from Example 15 was measured by relaxometry, the actual quantities of gadolinium being measured by ICP, on a Varian 710-ES instrument. A relaxivity $r_1$ (of the gadolinium species)=11.4 s⁻¹ mM⁻¹ (of gadolinium)⁻¹·s⁻¹ at 50 MHz is obtained, or about three times higher than that of the Gd-DOTA complex alone (adjusted to the gadolinium species), which is 3.8 s⁻¹ mM⁻¹ (of gadolinium)⁻¹·s⁻¹ at 50 MHz.

EXAMPLE 17

Synthesis of Coreless Nanoparticles Functionalized with DOTAGA Anhydride, in Two Successive Steps Nanoparticles are synthesized according to the protocol described in Example 8, but the surface functionalization is performed with a quantity of DOTAGA equal to 0.6 DOTAGA/Gd.

A solution of 240 mL of water containing DTPA in very large excess was prepared. The pH of the solution was adjusted to 6.5. This solution was added to 160 mL of the solution of nanoparticles. The mixture was stirred for 48 h. Thus, the free DTPA in very large excess made it possible to dissolve the core of the particles by forced complexing.

Figure 32:
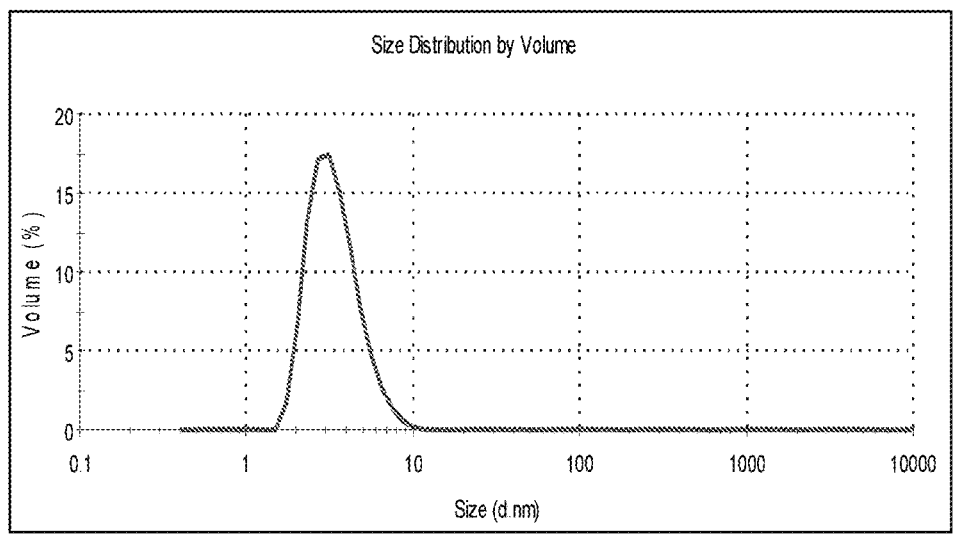

The solution was then purified by tangential filtration. The large size impurities were removed by filtration by means of a syringe, through a 0.2 μm membrane. The attached FIG. 32 shows the size distribution of the particles functionalized with DOTAGA anhydride, measured in water by PCS; mean value: 3.5 nm.

The solution of nanoparticles can be stored for several months in a refrigerator after lyophilization.

Moreover, the relaxivity of the particles was measured by relaxometry, the actual quantities of gadolinium being measured by ICP. A relaxivity $r_1$ (of the gadolinium species)=11.8 s⁻¹ mM⁻¹ (of gadolinium)⁻¹·s⁻¹ at 50 MHz is obtained, or about three times higher than that of the Gd-DOTA complex alone (adjusted to the gadolinium species), which is 3.8 s⁻¹ mM⁻¹ (of gadolinium)⁻¹·s⁻¹ at 50 MHz.

EXAMPLE 18

Synthesis of Lutetium Oxide Cores

A solution is prepared by dissolving a quantity of 2.25 g of lutetium chloride salt (LuCl₃, 6H₂O) in a volume of 245 mL of DEG. 245 mL of a soda solution at 0.08 mol/L in DEG is added to the solution obtained, at room temperature, in 10 h.

Figure 26:
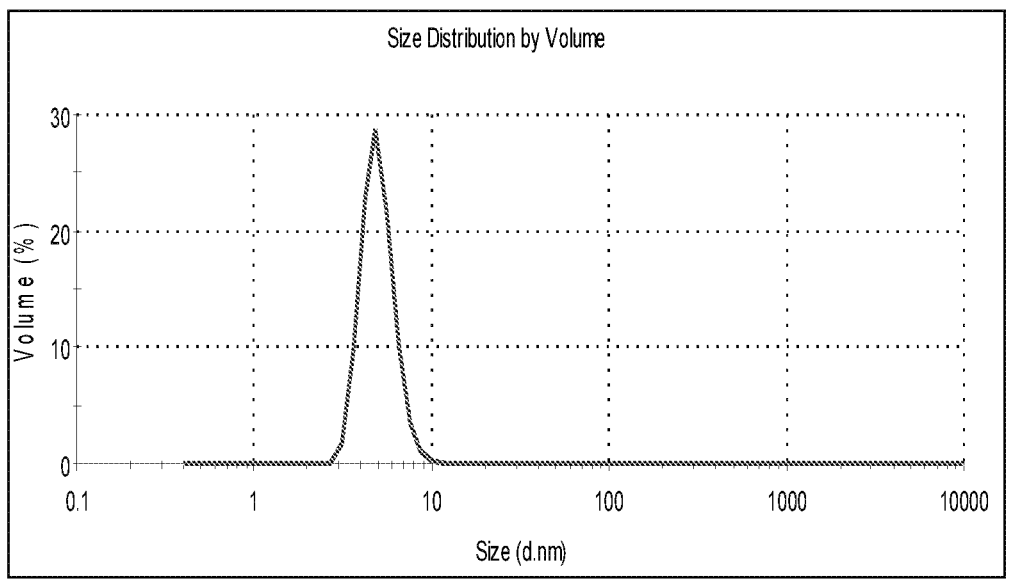

The final size of the nanoparticles is about 5 nm. The attached FIG. 26 shows the size distribution of the lutetium oxide cores, measured in DEG by PCS; mean value: 5.0 nm.

EXAMPLE 19

Functionalization of the Lutetium Oxide Cores with DTPABA

The 490 mL of solution of lutetium cores from Example 18 is diluted by two, with 490 mL of DEG. A layer of functionalized polysiloxane is synthesized by the sol-gel process around these cores. For this purpose, the solution of cores is heated to 40° C. in an oil bath, with stirring. 811 μL of APTES, 516 μL of TEOS and 1965 μL of an aqueous solution of triethylamine at 0.1 mol/L are added to the solution of cores. The solution is then stirred at 40° C. for 48 h.

Figure 27:
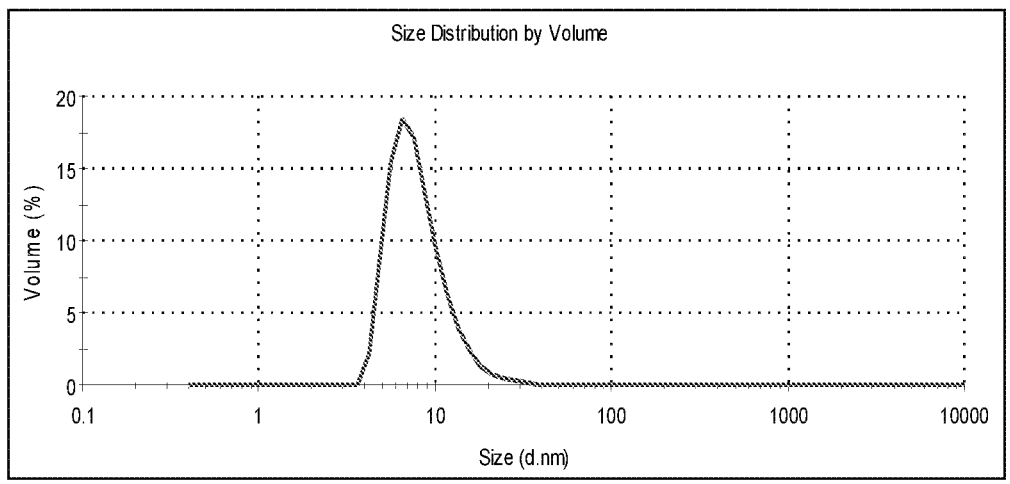

Core-shell particles are obtained with a size of about 8 nm, with amine functions on the surface. The attached FIG. 27 shows the size distribution of the polysiloxane-coated lutetium oxide cores; mean value: 8.3 nm.

Next, 0.1 g of DTPABA is dispersed in 2 mL of DMSO. Then 12 mL of the solution of cores is added to the solution of DTPABA. The mixture is stirred for 24 h.

Figure 28:
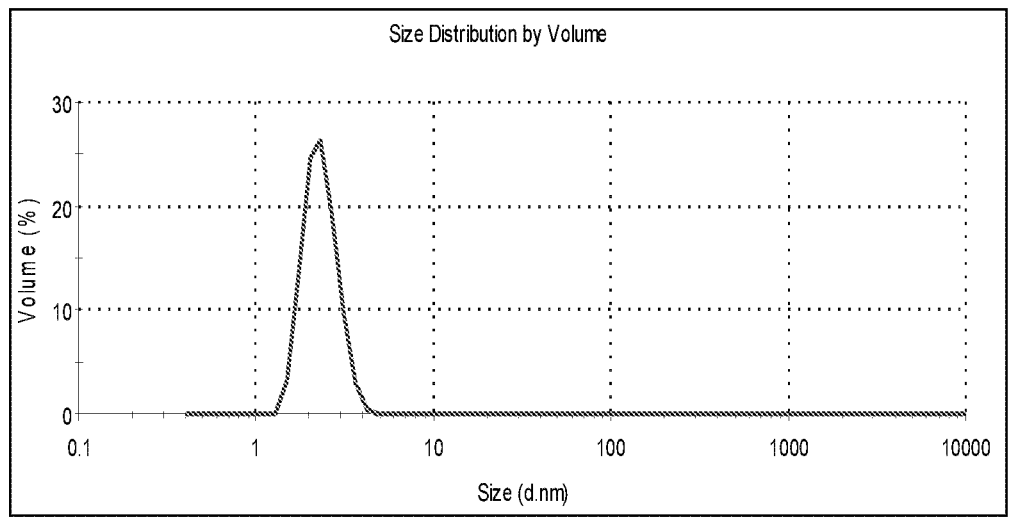

The nanoparticles are then precipitated in 100 mL of acetone. Then the acetone is removed, and the particles are redispersed in 20 mL of water. They are then purified by tangential filtration. Particles are obtained with a size of about 2.5 nm. The DTPABA, in large excess relative to the lutetium (4 DTPABA/Lu), has partly dissolved the core of the particles, hence their small size. The attached FIG. 28 shows the size distribution of the particles functionalized with DTPA; mean value: 2.4 nm.

The solution of nanoparticles can be stored for several months in a refrigerator after lyophilization.

EXAMPLE 20

Complexing the Lutetium Oxide Particles with Gd³⁺ Ions

Gadolinium chloride is dissolved in water, and the pH of the solution is adjusted to 6. The Gd³⁺ ions thus obtained are added to the lutetium particles from Example 19, in excess. The solution is stirred for 24 h. The solution is purified by tangential filtration in order to remove any Gd³⁺ ions that have not become attached to the molecules of DTPABA.

The initial particles of lutetium did not show any signal in relaxometry. However, after treatment with the Gd³⁺ ions, a signal of $T_1$=130 ms appears in relaxometry, after ten-fold dilution of the solution. This observation confirms the presence of molecules of DTPABA grafted on the particles, which have formed complexes with the Gd³⁺ ions added to the solution.

The invention claimed is:

1. A nanoparticle comprising
   (i) a polyorganosiloxane (POS) matrix,
   (ii) a metallic cation Gd³⁺,
   (iii) a chelating graft C¹ which is obtained by functionalizing said POS matrix of the nanoparticle with DOTAGA anhydride of the following formula:

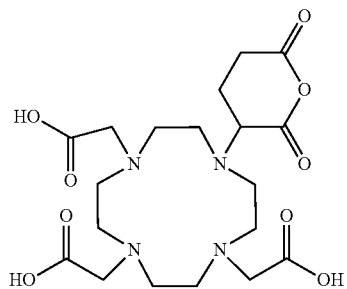

wherein Gd³⁺ is complexed to the chelating graft C¹, wherein a diameter $d_1$ of said nanoparticle is from 1 to 8 nm, said nanoparticle molecular weight (in kDa) is greater than or equal to 2 and less than or equal to 200, and wherein said nanoparticle does not comprise a crystallized core of gadolinium oxide.

2. The nanoparticle of claim 1, wherein the atom-% ratio ((Gd/Si)×100) is comprised between 10 and 60.

3. The nanoparticle of claim 1, wherein the diameter $d_1$ of said nanoparticle is from 1 to 5 nm.

4. The nanoparticle according to claim 1, wherein an atom % ratio (Gd/Si) is from 10 to 60.

5. The nanoparticle according to claim 1, wherein said chelating graft $C^1$ is in excess relative to said metallic cation $Gd^{3+}$.

6. The nanoparticle according to claim 1, wherein the nanoparticle further comprises another functionalizing graft Gf* bound to said POS matrix by an —Si—C—covalent bond, where Gf* can be derived from:
   a hydrophilic compound,
   a compound having an active ingredient PA1,
   a targeting compound,
   a luminescent compound.

7. The nanoparticle according to claim 1, wherein a relaxivity $r_1$ per $Gd^{3+}$ ion is greater than 5 $mM^{-1}$(of $Gd^{3+}$ ion)·$s^{-1}$ for a frequency of 20 MHz.

8. The nanoparticle according to claim 1, wherein a relaxivity $r_1$ per $Gd^{3+}$ ion at 60 MHz is greater than relaxivity $r_1$ per $Gd^{3+}$ ion at 20 MHz.

9. A suspension of a nanoparticle according to claim 1.

10. A solid material obtained by removal of the liquid, optionally by lyophilization, of said suspension according to claim 9.

11. An injectable liquid comprising a nanoparticle according claim 1.

12. An injectable liquid comprising a suspension according to claim 9.

13. An injectable liquid prepared from the solid material according to claim 10.

* * * * *

UNITED STATES PATENT AND TRADEMARK OFFICE
CERTIFICATE OF CORRECTION

| | | |
|---|---|---|
| PATENT NO. | : 11,497,818 B2 | Page 1 of 1 |
| APPLICATION NO. | : 15/987500 | |
| DATED | : November 15, 2022 | |
| INVENTOR(S) | : Lux et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this
Sixteenth Day of July, 2024

*Katherine Kelly Vidal*
Katherine Kelly Vidal
*Director of the United States Patent and Trademark Office*